United States Patent
Hamed

(10) Patent No.: US 10,792,338 B2
(45) Date of Patent: Oct. 6, 2020

(54) ERYTHROPOIETIN AND FIBRONECTIN COMPOSITIONS FOR THERAPEUTIC AND COSMETIC APPLICATIONS

(71) Applicant: Remedor Biomed Ltd., Nazareth Illit (IL)

(72) Inventor: Saher Hamed, Nazareth Illit (IL)

(73) Assignee: Remedor Biomed Ltd., Nazareth Illit (IL)

( * ) Notice: Subject to any disclaimer, the term of this patent is extended or adjusted under 35 U.S.C. 154(b) by 11 days.

(21) Appl. No.: 14/882,608

(22) Filed: Oct. 14, 2015

(65) Prior Publication Data

US 2016/0030525 A1    Feb. 4, 2016

Related U.S. Application Data

(60) Division of application No. 14/176,257, filed on Feb. 10, 2014, now abandoned, which is a continuation of application No. 12/673,519, filed as application No. PCT/IL2008/001119 on Aug. 13, 2008, now abandoned.

(60) Provisional application No. 61/064,311, filed on Feb. 27, 2008, provisional application No. 60/935,497, filed on Aug. 16, 2007.

(51) Int. Cl.

| | |
|---|---|
| *C07K 14/505* | (2006.01) |
| *C07K 14/78* | (2006.01) |
| *A61K 38/18* | (2006.01) |
| *A61K 38/39* | (2006.01) |
| *A61K 9/00* | (2006.01) |
| *A61K 9/06* | (2006.01) |
| *A61K 31/198* | (2006.01) |
| *A61K 31/21* | (2006.01) |
| *A61K 31/70* | (2006.01) |
| *A61K 38/19* | (2006.01) |
| *A61K 38/22* | (2006.01) |
| *A61K 38/36* | (2006.01) |
| *A61K 38/43* | (2006.01) |
| *A61K 47/32* | (2006.01) |

(52) U.S. Cl.
CPC ............ *A61K 38/39* (2013.01); *A61K 9/0014* (2013.01); *A61K 9/06* (2013.01); *A61K 31/198* (2013.01); *A61K 31/21* (2013.01); *A61K 31/70* (2013.01); *A61K 38/1816* (2013.01); *A61K 38/19* (2013.01); *A61K 38/22* (2013.01); *A61K 38/36* (2013.01); *A61K 38/43* (2013.01); *A61K 47/32* (2013.01)

(58) Field of Classification Search
None
See application file for complete search history.

(56) References Cited

U.S. PATENT DOCUMENTS

| | | | | |
|---|---|---|---|---|
| 4,929,442 A | * | 5/1990 | Powell | A61K 38/17 424/85.1 |
| 5,124,155 A | | 6/1992 | Reich | |
| 5,264,214 A | | 11/1993 | Rhee et al. | |
| 5,514,647 A | * | 5/1996 | Horowitz | A47B 7/02 514/2.4 |
| 5,840,691 A | | 11/1998 | Furcht et al. | |
| 6,420,394 B1 | * | 7/2002 | Supersaxo | A61K 9/0014 514/338 |
| 6,458,889 B1 | | 10/2002 | Trollsas et al. | |
| 6,913,762 B2 | | 7/2005 | Caplice et al. | |
| 7,166,570 B2 | | 1/2007 | Hunter et al. | |
| 7,235,525 B2 | | 6/2007 | Motomiya et al. | |
| 7,241,736 B2 | | 7/2007 | Hunter et al. | |
| 7,285,266 B2 | | 10/2007 | Vournakis et al. | |
| 7,312,198 B2 | | 12/2007 | Kiss | |
| 7,459,152 B2 | | 12/2008 | Sortwell et al. | |
| 7,473,678 B2 | | 1/2009 | Lynh | |
| 7,622,299 B2 | | 11/2009 | Sanders et al. | |
| 7,651,684 B2 | | 1/2010 | Hedrick et al. | |
| 7,745,387 B2 | | 6/2010 | Bahlmann et al. | |
| 7,910,547 B2 | | 3/2011 | Bader | |
| 8,022,234 B2 | | 9/2011 | Frincke et al. | |
| 8,178,745 B2 | | 5/2012 | Bader | |

(Continued)

FOREIGN PATENT DOCUMENTS

| | | |
|---|---|---|
| DE | 103 03 584 A1 | 8/2004 |
| EP | 1 550 715 A1 | 7/2005 |

(Continued)

OTHER PUBLICATIONS

Lewis et al. Topical therapies for glaucoma: what family physicians need to know. Abstract. American family physician, vol. 59, No. 7, pp. 1871-1879, 1882 (Apr. 1999). (Year: 1999).*
McCluskey et al. Topical fibronectin therapy in persistent corneal ulceration. Australian and New Zealand Journal of Ophthalmology. vol. 15: 257-262; (1987). (Year: 1987).*
Aicher, et al. "Mobilizing Endothelial Progenitor Cells", J. Hypertension, 45 (2005), pp. 321-325.
Bader, et al. "Interactive Role of Trauma Cytokines and Erythropoietin and Their Therapeutic Potential for Acute and Chronic Wounds", Rejuvination Research, vol. 14, No. 1 (2011), pp. 57-66.

(Continued)

*Primary Examiner* — Elizabeth C. Kemmerer
*Assistant Examiner* — Regina M DeBerry
(74) *Attorney, Agent, or Firm* — Norton Rose Fulbright US LLP; James R. Crawford

(57) ABSTRACT

A method of promoting wound healing or connective tissue reconstruction and a method of treating ischemia in a subject in need thereof are disclosed. The methods comprising topically administering to the subject about 10-30 mg per $cm^2$ wound tissue of Erythropoietin and about 100-300 mg per $cm^2$ wound tissue of Fibronectin, thereby promoting wound healing or connective tissue reconstruction or treating ischemia in the subject. Unit dosage forms, pharmaceutical compositions, cosmetic compositions and formulations comprising Erythropoietin and/or Fibronectin are also disclosed.

1 Claim, 21 Drawing Sheets

(56) References Cited

U.S. PATENT DOCUMENTS

| | | |
|---|---|---|
| 8,246,947 B2 | 8/2012 | Hedrick et al. |
| 8,252,817 B2 | 8/2012 | Flamme et al. |
| 8,361,781 B2 | 1/2013 | Morgan et al. |
| 8,377,864 B2 | 2/2013 | Catelas et al. |
| 8,771,678 B2 | 7/2014 | Hedrick et al. |
| 8,802,083 B2 | 8/2014 | Vournakis et al. |
| 9,012,393 B2 | 4/2015 | Catelas et al. |
| 2002/0016295 A1* | 2/2002 | Gentz ............ A61K 38/1825 514/9.2 |
| 2002/0160033 A1 | 10/2002 | Caplice et al. |
| 2003/0068297 A1 | 4/2003 | Jain |
| 2003/0072737 A1 | 4/2003 | Brines et al. |
| 2003/0147825 A1* | 8/2003 | Chiarelli ............... A61K 8/06 424/70.11 |
| 2003/0211130 A1 | 11/2003 | Sanders et al. |
| 2003/0219392 A1 | 11/2003 | Kung et al. |
| 2003/0219429 A1 | 11/2003 | Budny |
| 2004/0220140 A1 | 11/2004 | Vournakis et al. |
| 2004/0265268 A1* | 12/2004 | Jain ..................... A61K 8/64 424/85.1 |
| 2005/0025755 A1 | 2/2005 | Hedrick et al. |
| 2005/0142163 A1 | 6/2005 | Hunter et al. |
| 2005/0147562 A1 | 7/2005 | Hunter et al. |
| 2005/0147599 A1 | 7/2005 | Hunter et al. |
| 2005/0147645 A1 | 7/2005 | Hunter et al. |
| 2005/0148512 A1 | 7/2005 | Hunter et al. |
| 2005/0158274 A1 | 7/2005 | Hunter et al. |
| 2005/0169958 A1 | 8/2005 | Hunter et al. |
| 2005/0169959 A1 | 8/2005 | Hunter et al. |
| 2005/0175657 A1 | 8/2005 | Hunter et al. |
| 2005/0176635 A1 | 8/2005 | Hunter et al. |
| 2005/0186247 A1 | 8/2005 | Hunter et al. |
| 2005/0187158 A1 | 8/2005 | Ranby |
| 2005/0191248 A1 | 9/2005 | Hunter et al. |
| 2005/0208099 A1 | 9/2005 | Caplice et al. |
| 2005/0272634 A1 | 12/2005 | Bahlmann et al. |
| 2006/0166885 A1 | 7/2006 | Van Bekkum |
| 2006/0240063 A9 | 10/2006 | Hunter et al. |
| 2006/0240064 A9 | 10/2006 | Hunter et al. |
| 2007/0014777 A1 | 1/2007 | Kiss |
| 2007/0129282 A1 | 6/2007 | Ahlem et al. |
| 2007/0161552 A1 | 7/2007 | Bahlmann et al. |
| 2007/0254833 A1 | 11/2007 | Hunter et al. |
| 2007/0275936 A1 | 11/2007 | Ahlem et al. |
| 2008/0026064 A1 | 1/2008 | Vournakis et al. |
| 2008/0031850 A1 | 2/2008 | Bader |
| 2008/0113027 A1* | 5/2008 | Asgharian ............ A61K 9/0019 424/484 |
| 2009/0018033 A1 | 1/2009 | Morgan et al. |
| 2009/0018481 A1 | 1/2009 | Bader |
| 2009/0068255 A1* | 3/2009 | Yu ..................... A61K 8/0212 424/450 |
| 2010/0035906 A1 | 2/2010 | Flamme et al. |
| 2010/0247450 A1 | 9/2010 | Bader |
| 2010/0247451 A1 | 9/2010 | Bader |
| 2010/0247452 A1 | 9/2010 | Bader |
| 2010/0278916 A1 | 11/2010 | Bader |
| 2010/0310626 A1 | 12/2010 | Hamed |
| 2011/0172150 A1 | 7/2011 | Bader |
| 2012/0142589 A1 | 6/2012 | Brines et al. |
| 2012/0322772 A1 | 12/2012 | Flamme et al. |
| 2013/0236432 A1 | 9/2013 | Bader |

FOREIGN PATENT DOCUMENTS

| | | |
|---|---|---|
| EP | 1 517 988 B1 | 5/2013 |
| JP | 2007-517001 A | 6/2007 |
| WO | 2005/063965 A1 | 7/2005 |
| WO | 2007/055760 A2 | 5/2007 |
| WO | 2009/022238 A2 | 2/2009 |
| WO | 2009/083203 A2 | 7/2009 |
| WO | 2009/093240 A1 | 7/2009 |

OTHER PUBLICATIONS

Caneva Soumetz, et al. "Human Osteoblast-Like Cells Response to Nanofunctionalized Surfaces for Tissue Engineering", J. Biochemical Materials Research, Part B: Applied Biomaterials, 84B(1), (2007), pp. 249-255.

Chong, et al. "Erythropoietin: Cytoprotection in Vascular and Neuronal Cells", Current Drug Tragerts—Cardiovascular & Haematological Disorders, 3 (2003), pp. 141-154.

Dennis, et al. "Porous Ceramic Vehicles for Rat-marrow-derived (Rattus norvegicus) Osteogenic Cell DeliveryL Effects of Pretreatment with Fibronectin or Laminin", J. Oral Implantology, vol. XIX, No. 2 (1993), pp. 106-114.

Dunn, Jared M. "Local Wound Care in the Diabetic", Clinics in Podiatric Medicine and Surgery, vol. 4, No. 2 (1987), pp. 413-418.

Fu, et al. "Healing of chronic cutaneous wounds by topical treatment with basic fibroblast growth factor", Chinese Medical Journal in English, 115(3), (2002), pp. 331-335.

Fukuda, et al. "Fibronectin in the Tear Film", Investigative Ophthalmology & Visual Science, 37, No. 2 (1996), pp. 459-467.

Galeano, et al. "Recombinant Human Erythropoietin Stimulates Angiogenesis and Wound Healing in the Genetically Diabetic Mouse", Diabetes, vol. 53 (2004), pp. 2509-2517.

Grinnell, Frederick "Fibronectin and Wound Healing", J. Cell. Biochem., 26 (1984), pp. 107-116.

Grinnell, et al. "Degradation of Fibronectin and Vitronectin in Chronic Wound Fluid: Analysis by Cell Blotting, Immunoblotting, and Cell Adhesion Assays", J. Investigative Dermatol., 98 (1992), pp. 410-416.

Hamed, et al. "Topical Erythropoietin Promotes Wound Repair in Diabetic Rats", J. Investigative Dermatol., advance online publication (2009), www.jidonline.org, pp. 1-8.

Hamed, et al. "Erythropoietin Improves the Survival of Fat Tissue after Its Transplantation in Nude Mice", www.plosone.org, vol. 5, No. 11, (2010), pp. 1-12.

Henry, et al. "Vascular Endothelial Growth Factor in Ischemia for Vascular Angiogenesis", Circulation, 107 (2003), pp. 1359-1365.

Holstein, et al. "Erythropoietin (EPO)—EPO-receptor signaling improves early endochondral ossification and mechanical strength in fracture healing", Life Sciences, 80 (2007), pp. 893-900.

Ishiguro, et al. "Clonal Variability in β-Globin mRNA Content in an Interleukin-3-Dependent Bone Marrow Cell Line Transfected With the Erythropoietin Receptor Before and After Stimulation With Erythropoietin", J. Blood, vol. 90, No. 6 (1997), pp. 2273-2281.

Jimbo, et al. "The Pro-accelerative Effect of Plasma Fibronectin during Osseointegration", J. Japanese Society of Oral Implantology, 20(1), (2007), pp. 82-83: Abstract.

Jung, et al. "Recombinant tetra-cell adhesion motifs supports adhesion, migration and proliferation of keratinocytes/fibroblasts, and promotes wound healing", J. Experimental and Molecular Medicine, vol. 39, No. 5 (2007), pp. 663-672.

Kalfas, Iain H. "Principles of bone healing", Neurosurg. Focus, 10(4), (2001), pp. 1-4.

Katz, et al. "Erythropoietin treatment leads to reduced blood glucose levels and body mass: insights from murine models", J. Endocrinol. 205 (2010), pp. 87-95.

Kim, et al. "Clinical Efficacy of Topical Homologous Fibronectin in Persistent Corneal Epithelial Disorders", Korean J. Ophthalmol., 6 (1992), pp. 12-18.

Kim, et al. "Importance of the heparin-binding domain of fibronectin for enhancing cell adhesion activity of the recombinant fibronectin", Biotechnol. Lett., 28 (2006), pp. 1409-1413.

Kuramochi, et al. "Matrix metalloproteinase 2 improves the transplanted adipocyte survival in mice", European J. of Clinical Investigation, 38 (2008), pp. 752-759.

Kwon, et al."Topical Application of Plasma Fibronectin in Full-Thickness Skin Wound Healing in Rats", Experimental Biology and Medicine, 232(7), (2007), pp. 935-941.

Lei, et al. "Effect of rhVEGF gene transfection on survival of grafts after autologous free granular fat transplantation in rats", Chinese J. of Traumatology, 11(1), (2008), pp. 49-53.

Lipšic, et al. "Protective Effects of Erythropoietin in Cardiac Eschemia", J. Am. College of Cardiology, vol. 48, No. 11 (2006), pp. 2161-2167.

(56) References Cited

OTHER PUBLICATIONS

Lu, et al. "Improvement of the Survival if Human Autologous Fat Transplantation by Using VEGF-Transfected Adipose-Derived Stem Cells", Plastic and Reconstructive Surgery, 124 (2009), pp. 1437-1446.

McCulley, et al. "Topical Fibronectin Therapy of Persistent Corneal Epithelial Defects", Trans. Am. Ophthalmol. Soc., 91 (1993), pp. 367-390.

Nakano, et al. "Important Role of Erythropoietin Receptor to Promote VEFG Expression and Angiogenesis in Peripheral Ischemia in Mice", Circulation Research, 100 (2007), pp. 662-669.

Nisimura, et al. "Microvascular Angiogenesis and Apoptosis in the Survival of Free Fat Grafts", The Laringoscope, 110 (2000), pp. 1333-1338.

Pham, et al. "Native extracellular matrix coating on Ti surfaces", J. Biomed. Mater. Res., Part A, 66(2), (2003), pp. 310-316.

Pussell, et al. "Human Fibronectin Metabolism", J. Clin. Invest., 76 (1985), pp. 143-148.

Qiu, et al. "Effects of Plasma Fibronectin on the Healing of Full-Thickness Skin Wounds in Streptozotocin-Induced Diabetic Rats", J. Surgical Research, 138 (2007), pp. 64-70.

Ribatti, et al. "Human Erythropoietin Induces a Pro-Angiogenetic Phenotype in Cultured Endothelial Cells and Stimulates Neovascularization In Vivo", Blood, 193(8), (1999), pp. 2627-2636.

Rophael, et al. "Angiogenetic Growth Factor Synergism in a Murine Tissue Engineering Model of Angiogenesis and Adipogenesis", Am. J. Pathol., 171(6), (2007), pp. 2048-2057.

Sakai, et al. "Plasma fibronectin supports neuronal survival and reduces brain injury following transient focal cerebral ischemia but is not essential for skin-wound healing and hemostasis", Nature Medicine, vol. 7, No. 3 (2001), pp. 324-330.

Sengenes, et al. "Preadipocytes in the Human Subcutaneous Adipose Tissue Dispoay Distinct Features From the Adult Mesenchymal and Hematopietic Stem Cells", J. Cellular Physiol., 205 (2005), pp. 114-122.

Somervaille, et al. "Growth factor withdrawal from primary human erythroid progenitors induces apoptosis through a pathway involving glycogen synthase kinase-3 and Bax", Blood, 98(5), (2001), pp. 1374-1381.

Steed, et al. "Clinical evaluation of recombinant human platelet-derived growth factor for the treatment of lower extremity diabetic ulcers", J. Vascular Surgery, 21(1), (1995), pp. 71-78.

Takebe, et al. "Molecular and Cellular Analysis of Bone Formation at the Endosseous Implant Surfaces", Dental J. of the Iwate Med. Univ., 26(2), (2001), pp. 61-76: Abstract.

Tsiridis, et al. "Molecular aspects of fracture healing: Which are the important molecules?", Injury, Int. J. Care Injured, 38S1, (2007), pp. S11-S25.

Wang, et al. "Neural progenitor cells treated with EPO induce angiogenesis through the production of VEGF"m J. Cerebral Blood Flow & Metabolism, 28 (2008), pp. 1361-1368.

Weller, et al. "The effects of topical treatment with acidified nitrite on wound healing in normal an diabetic mice", Nitric Oxide, 15 (2006), pp. 395-399.

Westenbrink, et al. "Erythropoietin improves cardiac function through endothelial progenitor cell and vascular endothelial growth factor mediated neovascularization", European Heart J., 28 (2007), pp. 2018-2027.

Wysocki, et al. "Fibronectin Profiles in Normal and Chronic Wound Fluid", Laboratory Investigation, vol. 63, No. 6 (1990), pp. 825-831.

Xue, et al. "Effects of bovine plasma fibronectin in the proliferation and differentiation of rat osteoblasts", Chinese J. Shiyong Kougiang Yixue Zazhi, 20(6), (2004), pp. 730-732: Abstract.

Yi, et al. "VEFG gene therapy for the survival of transplanted fat tissue in nude mice", J. Plastic, Reconstructive & Aestetic Surgery, 60 (2007), pp. 272-278.

Zgang, Chi "Biocompatibility of ligament material by fibronectin surface modification", Chinese J. Zhongguo Zuzhi Gongcheng Yanjiy Yu Linchuang Kangfu 11(31), (2007), pp. 6149-6154: Absract.

Hamed, et al. "Fibronectin Potentiates Topical Erythropoietin-Induced Wound Repair in Diabetic Mice", J. of Investigative Dermatology, 131 (2011), pp. 1365-1374.

Buemi, et al. "Recombinant Human Erythropoietin Influences Revascularization and Healing in a Rat Model of Random Ischaemic Flaps", Acta Derm. Venerol., 82 (2002), pp. 411-417.

Buemi, et al. "Recombinant Human Erythropoietin Stimulates Angiogenesis and Healing of Ischemic Skin Wounds", Schocl, vol. 22, No. 2 (2004), pp. 169-173.

Crovetti, et al. "Platelet gel for healing cutaneous chronic wounds", Transfusion and Apheresis Science, 30 (2004), pp. 145-151.

\* cited by examiner

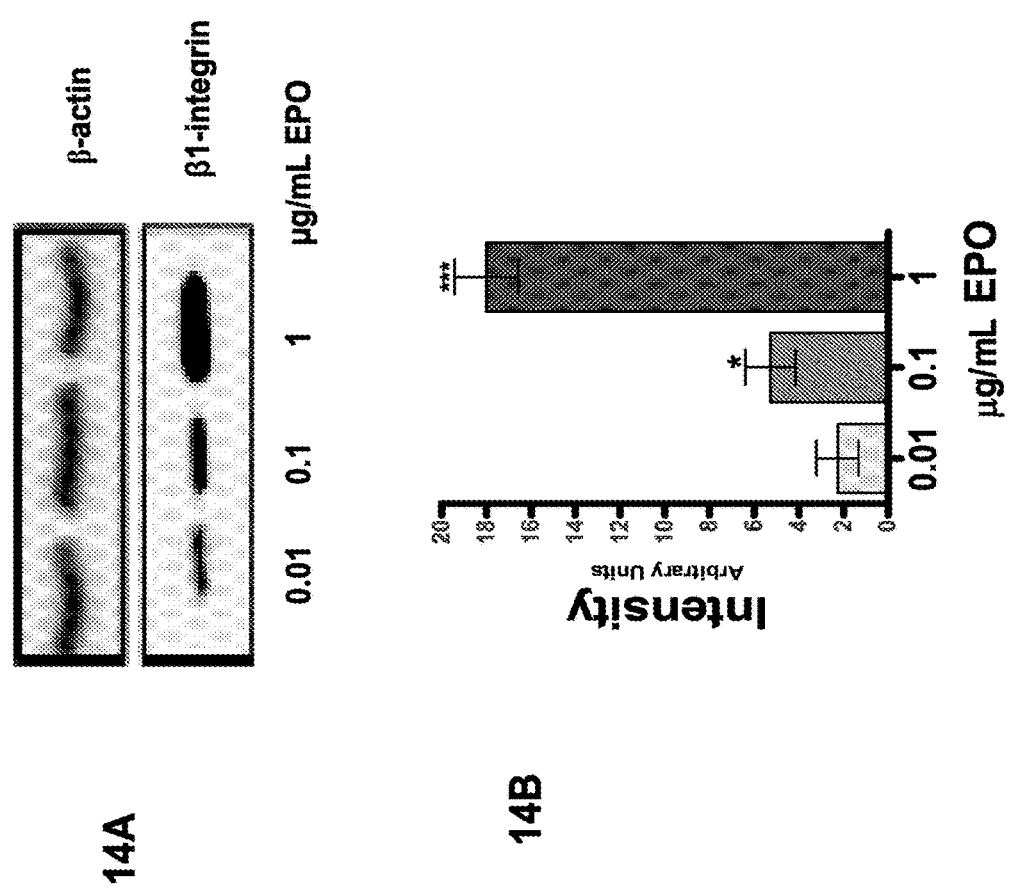
Figs. 14A-B

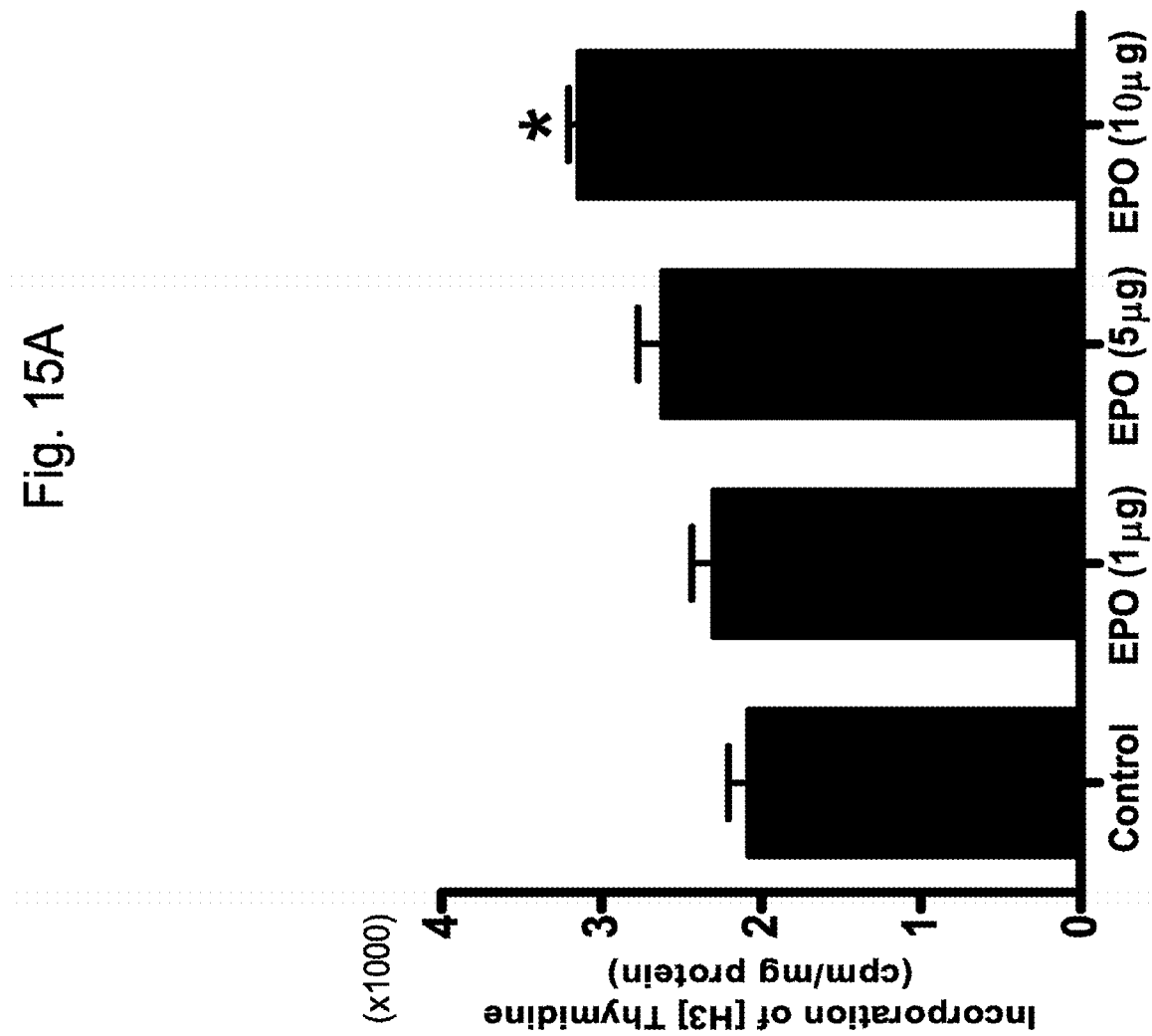

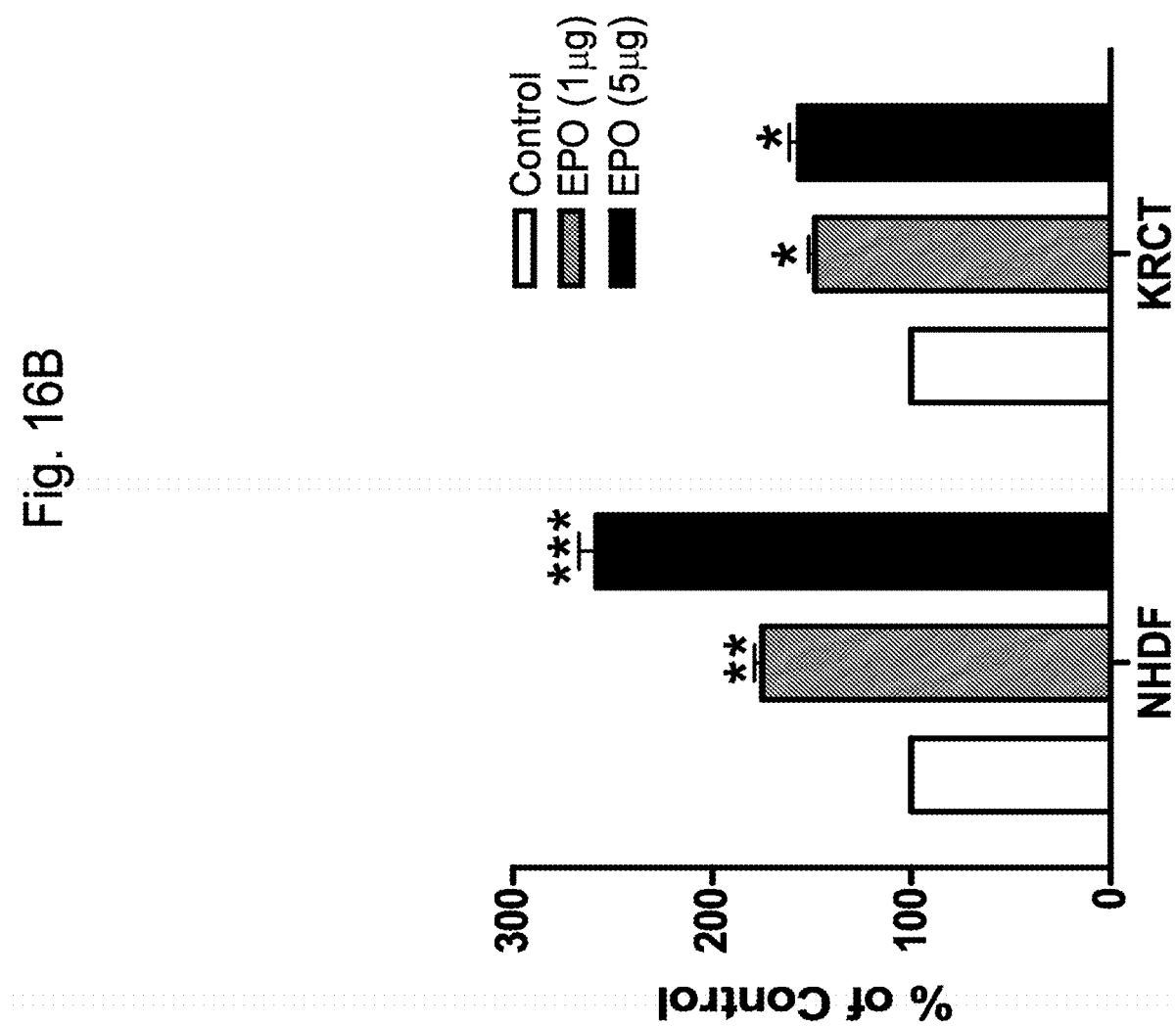

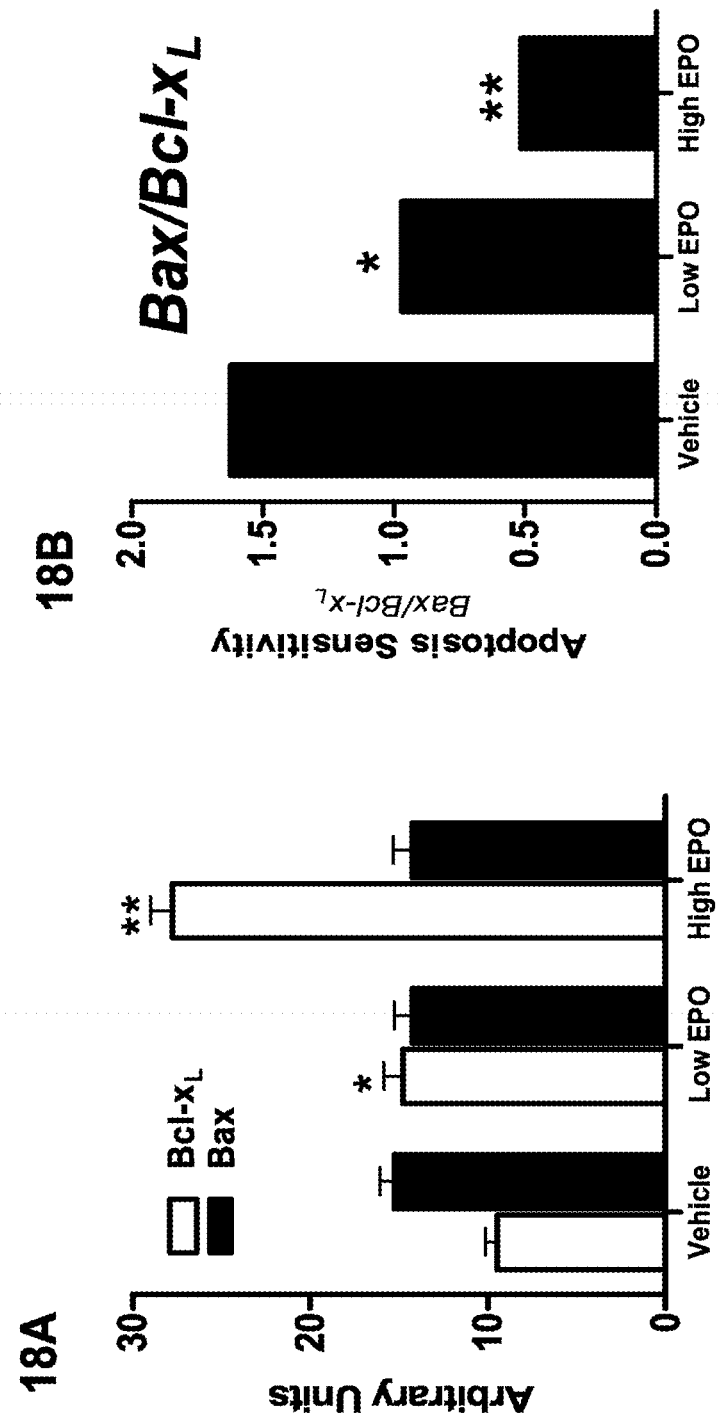
Figs. 18A-B

ERYTHROPOIETIN AND FIBRONECTIN COMPOSITIONS FOR THERAPEUTIC AND COSMETIC APPLICATIONS

RELATED APPLICATIONS

This application is a division of U.S. patent application Ser. No. 14/176,257, filed Feb. 10, 2014, which is a continuation of a U.S. patent application Ser. No. 12/673,519 filed Feb. 15, 2010, which is a § 371 of International Patent Application No. PCT/IL2008/001119 filed Aug. 13, 2008, which claims priority from U.S. Provisional Patent Application Nos. 61/064,311 filed Feb. 27, 2008 and 60/935,497 filed Aug. 16, 2007, each of which is incorporated herein by reference in its entirety for all purposes.

FIELD AND BACKGROUND OF THE INVENTION

The present invention, in some embodiments thereof, relates to Erythropoietin and Fibronectin compositions and, more particularly, but not exclusively, to the use of same in therapeutic and cosmetic applications.

The extracellular matrix (ECM), often referred to as the connective tissue, is a complex structural entity found within the mammalian tissue which surrounds and supports cells. The three major classes of ECM biomolecules are the structural proteins (e.g. collagen and elastin), specialized proteins (e.g. fibrillin, fibronectin and laminin) and proteoglycans [e.g. glycosaminoglycans (GAGs)].

Collagen, which makes up 75 percent of the skin, is the body's main structural protein and is produced mainly by fibroblasts. Healthy collagen levels are attributed to the smooth, plump appearance of young, healthy skin. However, the breakdown of healthy collagen, the decline in collagen production (e.g. by deceleration in the division rate of skin cells) and the defective cross-linking of collagen and elastin fibers in the skin, leads to the development of skin maladies and conditions including acne, actinic keratoses, photoaged skin, unwanted wrinkles and the appearance of aged skin (e.g. sags, changes in tone and texture). Collagen deposit is also a central event in the process of wound healing and scarring.

Wound healing is a complex process mediated by interactions between various cells (e.g. keratinocytes, fibroblasts and epidermal microvascular endothelial cells), growth factors, cytokines and mediators. This process is regulated by a pattern of events including inflammation, coagulation, neovascularization, collagen deposit, formation of granulation tissue, epithelialization, and tissue remodeling. During the wound healing process, various growth factors (e.g., vascular endothelial growth factor, platelets derived growth factor and fibroblast growth factor) are secreted to accelerate wound healing. In healthy individuals, the normal wound healing process is relatively short, occurs at an optimal rate and depends on the type and size of the wound. However, in patients with diabetes or with the classical skin maladies, wound healing is usually delayed or even impaired completely and consequently chronic wounds develop. This impaired process represents a major health-care problem with considerable socioeconomic impact.

Diabetes, caused by hyperglycemia, is a chronic disease that is associated with many complications including chronic wounds. The cellular and molecular mechanisms underlying diabetic-induced damaged wound healing are poorly understood. One contributing factor that may play a crucial role is poor subcutaneous blood supply. High blood glucose hinders proliferation of cells and decreases new blood vessel formation, thus, contributing to a reduction in the level of numerous mediators, factors and cofactors associated with wound healing (e.g. growth factors). Likewise, in diabetes, fibroblasts fail to produce extracellular matrix (ECM) and keratinocytes fail to induce reepithelialization. Furthermore, decreased collagen deposit, chemotaxis and the inhibition of fibroblast proliferation may all be associated with impairment of wound healing in diabetes Cutaneous wound healing including incisional, excisional, post surgical, pressure ulcers and burn wounds which are acute or chronic have paid the attention of various researchers. Many reports have suggested diverse techniques and materials in order to accelerate the healing of wounds, including wounds of diabetic patients, and local wound care, surgery, skin grafting, debridement, topical antibiotics and vascular reconstruction. Furthermore, systemic treatments and topical applications of a wide range of agents including fibroblast growth factor (FGF) [Fu et al., Chin Med J Engl. (2002) 115(3):331-5], platelet-derived growth factor (PDGF) [Steed, J Vasc Surg. (1995) 21(1): 71-8], platelet gel [Crovetti et al., Transfus Apher Sci. (2004) 30(2):145-51] and acidified nitrite [Weller and Finnen, Nitric Oxide (2006) 15(4):395-9] have been contemplate in an attempt to accelerate wound healing.

Erythropoietin (EPO), a glycoprotein hormone that is a cytokine for erythrocyte precursors in the bone marrow, is the hormone regulating red blood cell production. The EPO receptor is present on many cells, including endothelial cells, fibroblasts, hair follicle cells and keratinocytes, and thereby EPO functions directly to induce proliferation of endothelial cells, angiogenesis, production of extracellular matrix and reepithelialization. The ability of EPO to stimulate endothelial cell mitosis and motility may be of importance in neovascularization and wound healing [Buemi et al., Acta Derm Venereol. (2002) 82(6):411-7].

Fibronectin (FN) is a high-molecular-weight glycoprotein that binds cell membrane integrins and extracellular matrix components (e.g., collagen, fibrin, elastin and heparin). FN is involved in wound healing by contributing to hemostasis and phagocytosis, assisting in control of infection, promoting fibroblast migration and proliferation, enhancing epithelialization and organization of granulation tissue and, ultimately, by modifying the tensile strength of scar tissue [Grinnell, J Cell Biochem. (1984) 26(2):107-16]. Plasma FN has been demonstrated to be degraded in diabetic wounds [Wysocki and Grinnell, Lab Invest. (1990) 63(6):825-31] and impaired wound healing in diabetic rats was characterized by a reduction in plasma fibronectin at the wound site [Qiu et al., J Surg Res. (2007) 138(1):64-70].

Various approaches for treating wounds using EPO or FN and other uses of same in cosmetic applications have been attempted, some are summarized infra.

Administration of EPO for wound treatment has been described by Galeano et al. in a diabetic mouse wound model [Galeano et al., Diabetes. (2004) 53(9):2509-17]. According to their teachings, injection of recombinant human erythropoietin (rHuEPO) to diabetic mice improved the impaired wound healing and increased the wound-breaking strength.

U.S. Pat. No. 6,458,889 discloses a crosslinkable polymer composition which contains a minimum of three components (a polynucleophilic, a polyelectrophilic, and a nucleophilic component), each of which participates in a reaction that results in a crosslinked matrix. For instance, the crosslinkable polymer composition may be applied within a wound to promote tissue regrowth. The components of the crosslinkable composition are selected so that crosslinking gives rise to a biocompatible, non-immunogenic matrix. According to the teachings of U.S. Pat. No. 6,458,889, cytokines (such as EPO) can be incorporated with the collagen-polymer conjugate to aid in the treatment of wounds. Additionally, naturally occurring hydrophilic polymers (such as fibronectin) and cytokines (such as erythropoietin) can be incorporated with the collagen-polymer conjugate to aid in the treatment of scars and wrinkles.

Topical application of FN for wound treatment has been described by Qiu et al. in a diabetic rat model [Qiu et al., supra]. According to their teachings, topical application of FN significantly enhanced wound closure. Furthermore, FN-treated wounds showed increased fibroblast vascularization, collagen regeneration, and epithelialization.

PCT Publication No. WO07055760 discloses protein compositions for promoting wound healing and skin regeneration. The protein compositions comprise a combination of lactoferrin and alkaline phosphatase (such as placental alkaline phosphatase) and may include additional wound repair promoters (such as fibronectin) which can promote proliferation and survival of cells. According to the teachings of PCT Publication No. WO07055760, the protein compositions may be administered topically, by injection, or by other suitable means, and in addition to improving the quality of skin, may also be effective in reducing inflammation and microbial infection in the skin.

U.S. Publication No. 20070014777 discloses protein compositions for promoting wound healing, skin regeneration and to enhance the quality of skin. According to the teachings of U.S. Publication No. 20070014777, four proteins [alpha(1)-antitrypsin (AT), human placental alkaline phosphatase (PALP), human transferrin (TF), and alpha-1-acid glycoprotein (AGP)] were selected each of which has a different spectrum of cellular action and each positively affects the wound healing process in collaboration with the other proteins. Depending on the nature, size and location of the wound, compositions derived from these proteins can be enhanced by other agents (including FN or EPO) that are known to positively affect skin regeneration, quality of the skin and the wound healing process.

U.S. Publication No. 20030068297 discloses compositions for repairing and rejuvenating mammalian skin. These compositions contain cell growth enhancers (e.g. EPO or FN) to increase the growth rate of skin cells, nutrients (e.g. carbohydrates) to support log phase growth of skin cells, extracellular matrix proteins (e.g. integrins), stimulators of extracellular matrix proteins (e.g. adhesion proteins), and penetration enhancers (e.g. mineral oil). According to the teachings of U.S. Publication No. 20030068297, at least one component of each group must comprise the skin repair composition. The compositions are described for repairing wrinkles in the skin, for generating hair growth and for promoting healing of skin that has suffered a wound (such as a sunburn, cut, scrape, or abrasion).

U.S. Publication No. 20040265268 discloses compositions for repairing and rejuvenating mammalian skin. These compositions contain cell growth enhancers (e.g. EPO or FN) to increase the growth rate of skin cells, stimulators of cell growth enhancers (e.g. ascorbic acid), nutrients (e.g. carbohydrates) to support log phase growth of skin cells, cell protectors (e.g. insulin) to protect growing cells and enhanced cellular activity, antioxidants (e.g. Vitamin C) to protect rejuvenated cells, extracellular matrix proteins (e.g. adhesion molecules), stimulators of extracellular matrix proteins (e.g. adhesion proteins, FN), and penetration enhancers (e.g. lipoproteins). According to the teachings of U.S. Publication No. 20040265268, at least one component of each group must comprise the skin repair composition. The compositions are described for repairing wrinkles in the skin, for generating hair growth and for promoting healing of skin that has suffered a wound (such as a sunburn, cut, scrape, or abrasion).

SUMMARY OF THE INVENTION

According to an aspect of some embodiments of the present invention there is provided a method of promoting wound healing or connective tissue reconstruction in a subject in need thereof, the method comprising topically administering to the subject about 10-30 µg per $cm^2$ wound tissue of Erythropoietin and about 100-300 µg per $cm^2$ wound tissue of Fibronectin, thereby promoting wound healing or connective tissue reconstruction in the subject.

According to an aspect of some embodiments of the present invention there is provided a method of treating ischemia in a subject in need thereof, the method comprising topically administering to the subject about 10-30 µg per $cm^2$ tissue of Erythropoietin and about 100-300 µg per $cm^2$ tissue of Fibronectin, thereby treating ischemia in the subject.

According to some embodiments of the invention the connective tissue comprises collagen.

According to some embodiments of the invention, a dose of the Erythropoietin is about 20 µg per $cm^2$ tissue.

According to some embodiments of the invention, a dose of the Fibronectin is about 200 µg per $cm^2$ tissue.

According to some embodiments of the invention, administering is effected at least once a day.

According to some embodiments of the invention, the method further comprising administering a factor selected from the group consisting of an extracellular matrix component, a growth factor, a hormone, an angiogenic factor, a coagulation factor, a cytokine, a chemokine, an enzyme, a neurotransmitter, a vitamin, a carbohydrate, an ion, an iron chelator, a fatty acid, an antibiotic, and an amino acid.

According to some embodiments of the invention, the wound is inflicted by diabetes.

According to some embodiments of the invention, the wound is a chronic wound.

According to some embodiments of the invention, the wound is an acute wound.

According to some embodiments of the invention, the wound is selected from the group consisting of an ulcer, a burn and a surgical wound.

According to some embodiments of the invention, the subject is a human being.

According to some embodiments of the invention, promoting connective tissue reconstruction is effected in a skin condition or malady.

According to some embodiments of the invention, the skin condition or malady is selected from the group consisting of a sag, a fine line, a wrinkle, an age spot, a photo damage, a blemish, a dry skin, an acne, a sore and a wart.

According to some embodiments of the invention, administering of the Erythropoietin and the Fibronectin is effected concomitantly.

According to some embodiments of the invention, the Erythropoietin and the Fibronectin are in a co-formulation.

According to some embodiments of the invention, the Erythropoietin and the Fibronectin are in separate formulations.

According to an aspect of some embodiments of the present invention there is provided a unit dosage form comprising Erythropoietin at a dose of about 10-30 µg.

According to an aspect of some embodiments of the present invention there is provided a unit dosage form comprising Fibronectin at a dose of about 100-300 µg.

According to an aspect of some embodiments of the present invention there is provided a unit dosage form comprising Erythropoietin at a dose of about 10-30 µg and Fibronectin at a dose of about 100-300 µg.

According to an aspect of some embodiments of the present invention there is provided a pharmaceutical composition comprising as an active ingredient about 10-30 µg per ml Erythropoietin and a pharmaceutically acceptable carrier or diluent for topical administration.

According to an aspect of some embodiments of the present invention there is provided a pharmaceutical composition comprising as an active ingredient about 100-300 µg per ml Fibronectin and a pharmaceutically acceptable carrier or diluent for topical administration.

According to an aspect of some embodiments of the present invention there is provided a pharmaceutical composition comprising as an active ingredient about 10-30 µg per ml Erythropoietin and about 100-300 µg per ml Fibronectin and a pharmaceutically acceptable carrier or diluent for topical administration.

According to some embodiments of the invention, the unit dosage form is in a form selected from the group consisting of an adhesive bandage, a non-adhesive bandage, a wipe, a gauze and a pad.

According to some embodiments of the invention, the pharmaceutically acceptable carrier or diluent is selected from the group consisting of a cream, a gel, a spray, a lotion, an ointment, an oil, a wash and a spray.

According to some embodiments of the invention, the unit dosage form or pharmaceutical composition further comprising a factor selected from the group consisting of an extracellular matrix component, a growth factor, a hormone, an angiogenic factor, a coagulation factor, a cytokine, a chemokine, an enzyme, a neurotransmitter, a vitamin, a carbohydrate, an ion, an iron chelator, a fatty acid, an antibiotic, and an amino acid.

According to an aspect of some embodiments of the present invention there is provided a cosmetic composition comprising as an active ingredient about 10-30 µg per ml Erythropoietin and a cosmetically acceptable carrier or diluent.

According to an aspect of some embodiments of the present invention there is provided a cosmetic composition comprising as an active ingredient about 100-300 µg per ml Fibronectin and a cosmetically acceptable carrier or diluent.

According to an aspect of some embodiments of the present invention there is provided a cosmetic composition comprising as an active ingredient about 10-30 µg per ml Erythropoietin and about 100-300 µg per ml Fibronectin and a cosmetically acceptable carrier or diluent.

According to some embodiments of the invention, the cosmetically acceptable carrier or diluent is selected from the group consisting of a cream, a gel, a spray, a lotion, an ointment, an oil, a wash and a spray.

According to some embodiments of the invention, the cosmetic composition further comprising a factor selected from the group consisting of an extracellular matrix component, a growth factor, a hormone, an angiogenic factor, a coagulation factor, a cytokine, a chemokine, an enzyme, a neurotransmitter, a vitamin, a carbohydrate, an ion, an iron chelator, a fatty acid, an antibiotic, and an amino acid.

According to an aspect of some embodiments of the present invention there is provided a use of the unit dosage form or pharmaceutical composition for promoting wound healing.

According to some embodiments of the invention, the wound is a chronic wound.

According to some embodiments of the invention, the wound is an acute wound.

According to some embodiments of the invention, the wound is inflicted by diabetes.

According to some embodiments of the invention, the wound is selected from the group consisting of an ulcer, a burn and a surgical wound.

According to an aspect of some embodiments of the present invention there is provided a use of the unit dosage form or pharmaceutical composition for treating ischemia.

According to an aspect of some embodiments of the present invention there is provided a formulation, comprising: (i) as an active ingredient Erythropoietin and Fibronectin, wherein a concentration of the Erythropoietin is about 10-30 µg/mL and a concentration of the Fibronectin is about 100-300 µg/mL; (ii) about 0.20% Methyl Paraben; (iii) about 9% Laureth and Isoparafin and Polyacrylamide; (iv) about 12% Deionized Water; and (v) up to 100% Phosphate Buffer Solution.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
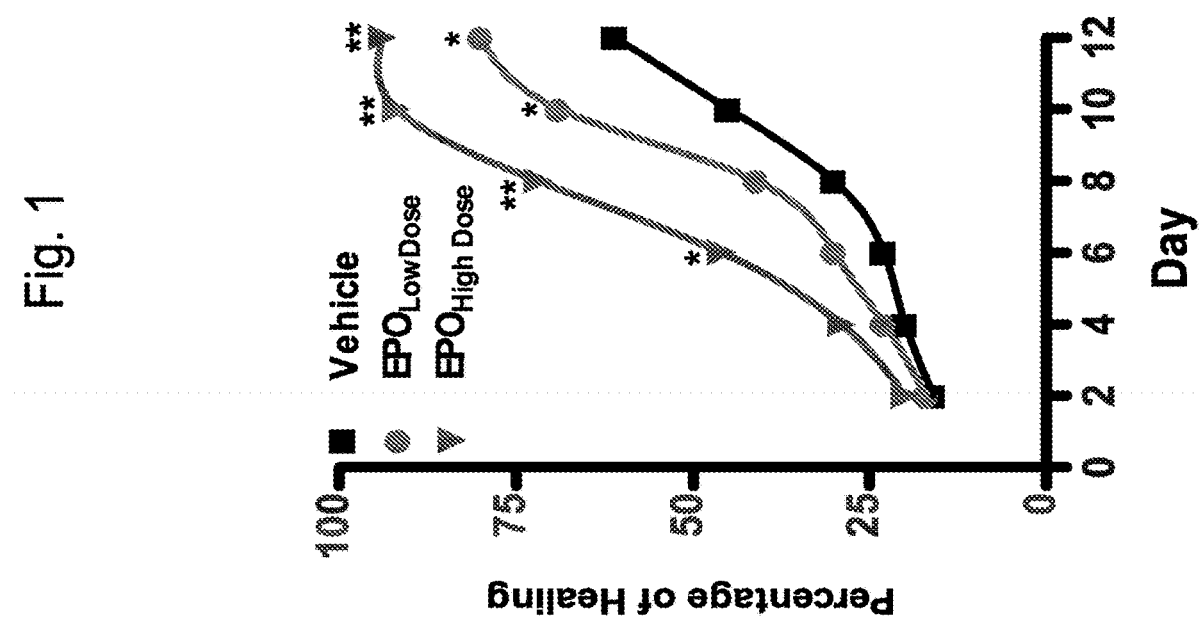

FIG. 1 is a line graph depicting quantitative assessment of wound healing and time to complete wound closure in diabetic rats. The graph shows the percentage of wound healing in diabetic rats 2, 4, 6, 8, 10 and 12 days after the beginning of treatment with vehicle alone (depicted by squares), with a cream containing low dose erythropoietin (EPO, depicted by circles) or with a cream containing high dose EPO (depicted by triangles). Of note, the results indicate a major difference between wound healing in rats treated with a cream containing high dose EPO compared to low dose EPO and control rats.

Figure 2:
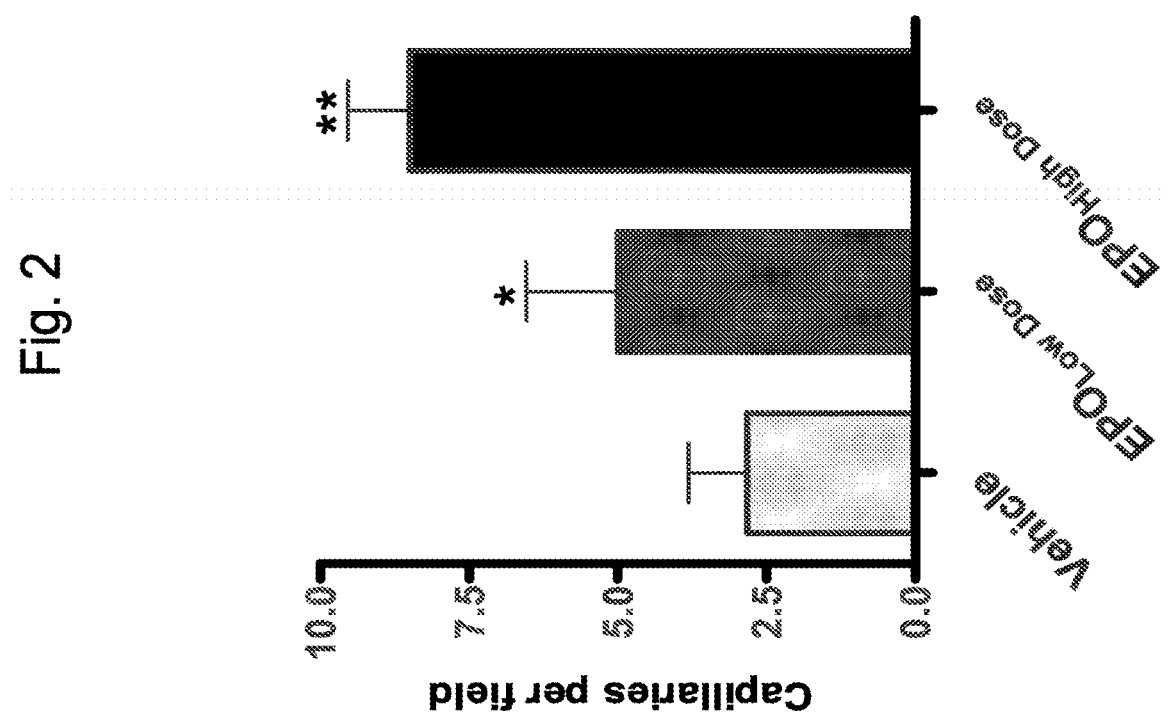

FIG. 2 is a bar graph depicting microvessel density (MVD) in wounds of diabetic rats at the end of treatment. The graph shows assessment of capillaries in tissue samples from wounds of rats treated with vehicle (left column), with a cream containing low dose EPO (middle column) or with a cream containing high dose EPO (right column) using immunohistochemical staining of CD31.

Figure 3:
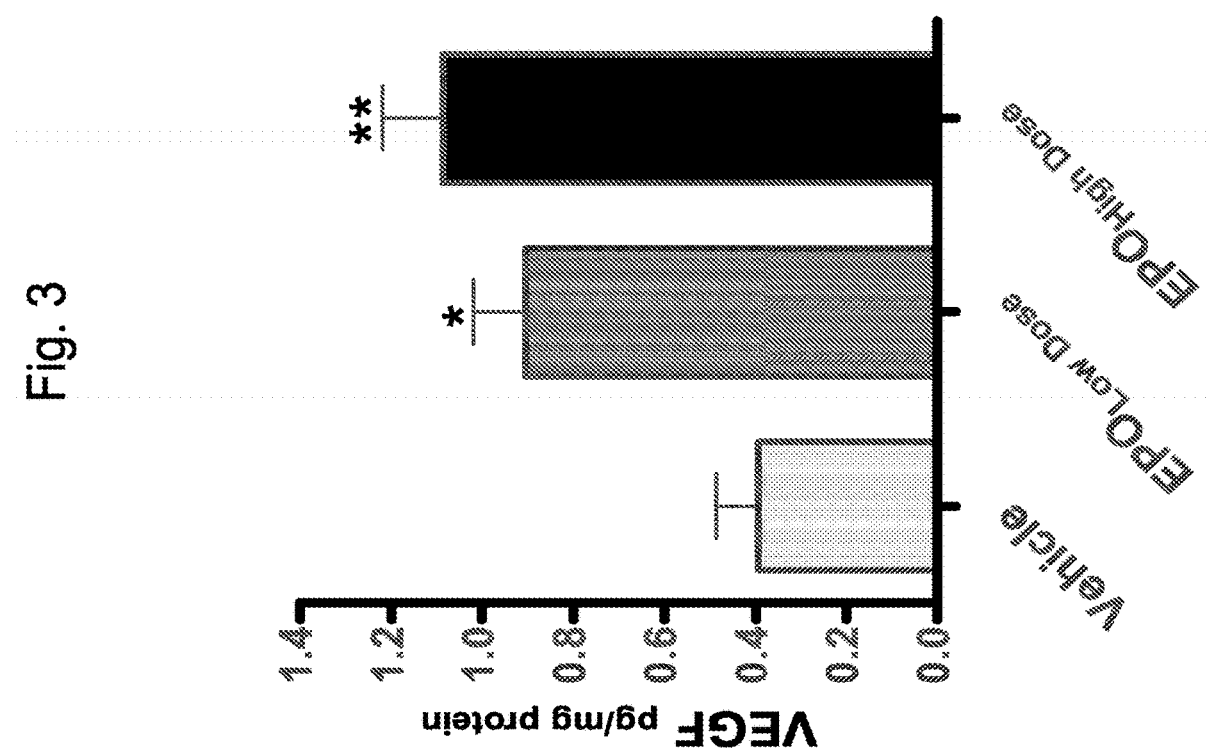

FIG. 3 is a bar graph depicting levels of the vascular endothelial growth factor (VEGF) in wounds of diabetic rats at the end of treatment. The graph shows VEGF content in tissue samples from wounds of rats treated with vehicle (left column), with a cream containing low dose EPO (middle column) or with a cream containing high dose EPO (right column).

Figure 4:
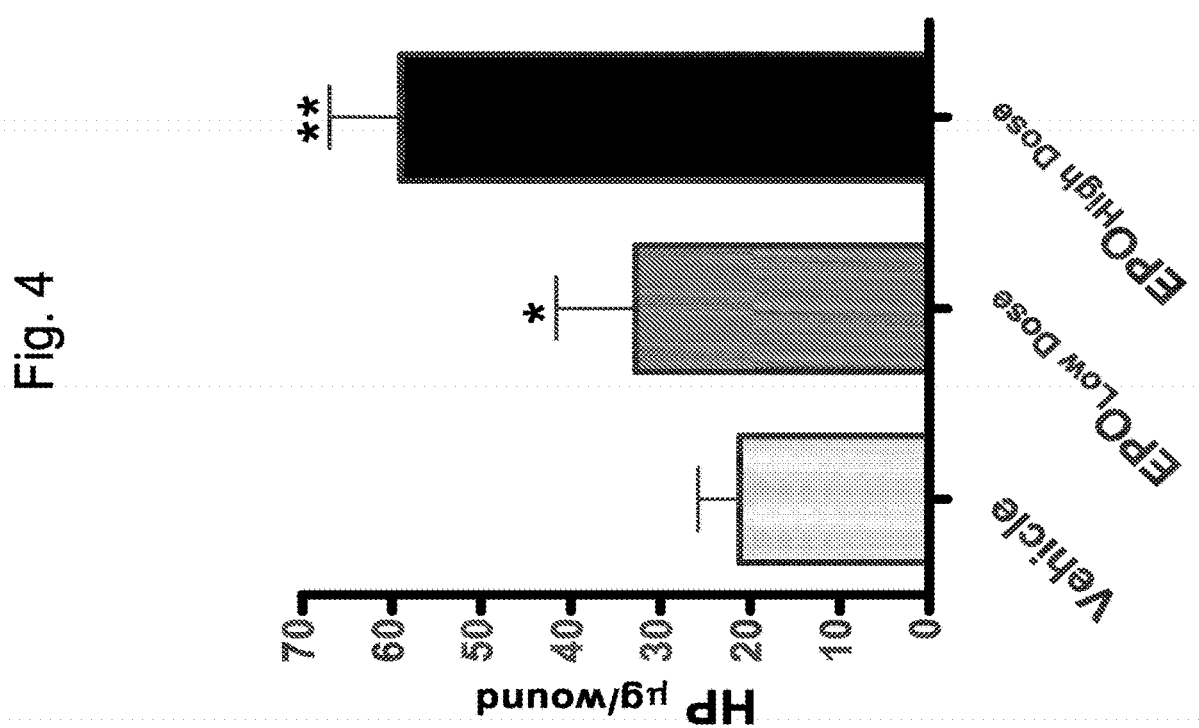

FIG. 4 is a bar graph depicting levels of Hydroxyproline (HP) in wounds of diabetic rats at the end of treatment. The graph shows HP content in tissue samples from wounds of rats treated with vehicle (left column), with a cream containing low dose EPO (middle column) or with a cream containing high dose EPO (right column).

Figure 5:
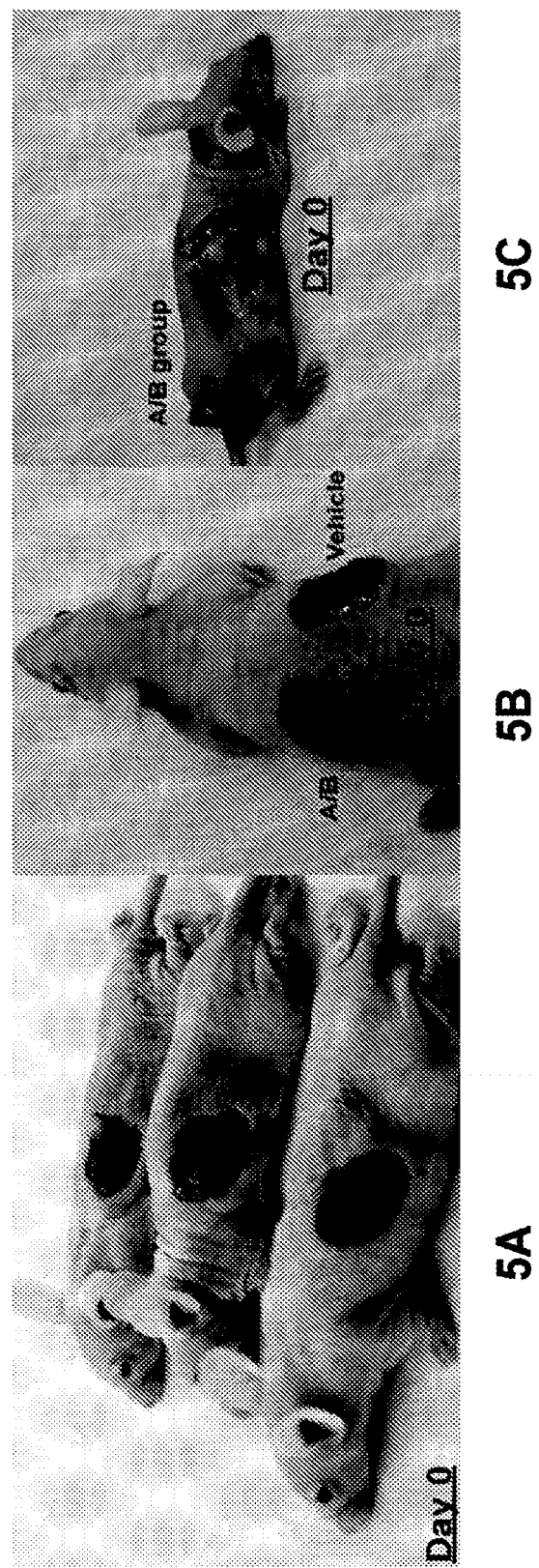

FIGS. 5A-C are photographs showing CD1 nude diabetic mice on day 0 of the experiment. FIG. 5A shows three representative mice on day 0 of the experiment wherein two full-thickness skin wounds (approximately 20 mm in diameter/wound) have been generated in the dorsal skin of the mice; FIG. 5B shows a representative mouse on day 0 of the experiment treated with a cream containing erythropoietin (EPO) and fibronectin (FN, designated A/B, on its left side) or with a basic cream (vehicle, on its right side); FIG. 5C shows a representative mouse on day 0 of the experiment treated with a cream containing EPO/FN (designated A/B).

Figure 6:
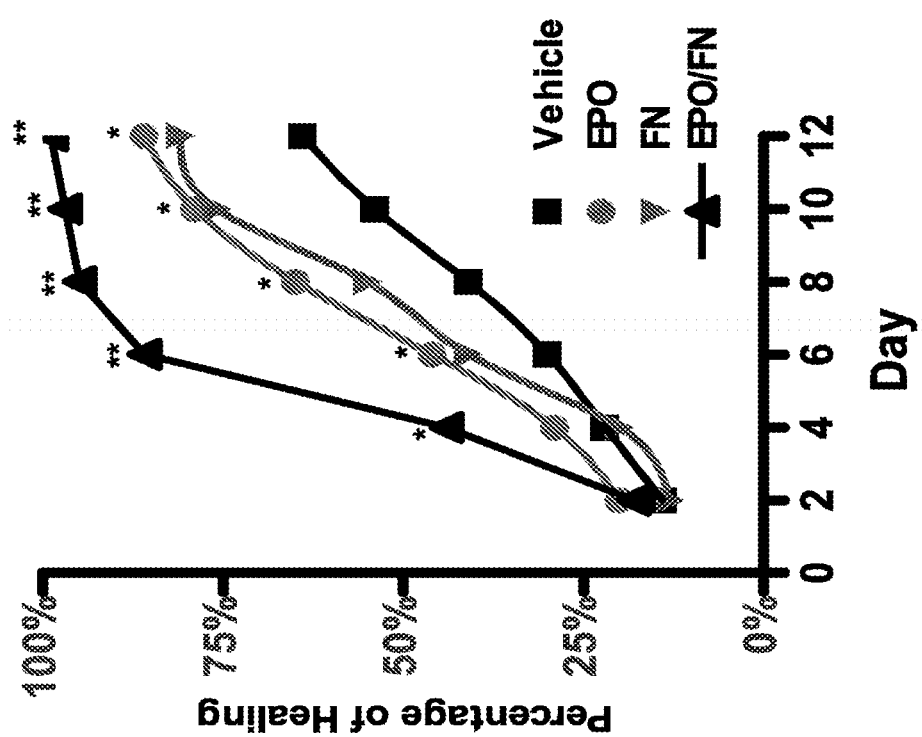

FIG. 6 is a line graph depicting quantitative assessment of wound healing and time to complete wound closure in diabetic CD1 nude mice. The graph shows the percentage of wound healing in diabetic CD1 nude mice 2, 4, 6, 8, 10 and 12 days after the beginning of treatment with vehicle alone (depicted by squares), with a cream containing only EPO (depicted by circles), with a cream containing only FN (depicted by upside down triangles) or with a cream containing both EPO and FN (depicted by triangles). Of note, the results indicate a major difference between wound healing in mice treated with the combination EPO/FN compared to EPO, FN and control mice.

Figure 7:

FIGS. 7A-D are pictures depicting CD1 nude diabetic mice on day 4 of the experiment. FIG. 7A shows three representative mice on day 4 of the experiment where the dorsal skin wounds have been treated with a cream containing only FN (middle mouse) or a cream containing both EPO and FN (the other two mice); FIG. 7B shows a representative mouse on day 4 of the experiment where the wound has been treated with vehicle (V); FIG. 7C shows a representative mouse on day 4 of the experiment where the wound has been treated with a cream containing both EPO and FN (A/B); and FIG. 7D shows 3 representative mice on day 4 of the experiment where the dorsal skin wounds have been treated with a cream containing only FN (middle mouse) or a cream containing both EPO and FN (the other two mice). Mice marked by A/B (treated with a cream containing both EPO and FN), marked by A (treated with a cream containing only EPO), marked by B (treated with a cream containing only FN) or marked by V (treated with a cream vehicle).

Figure 8:
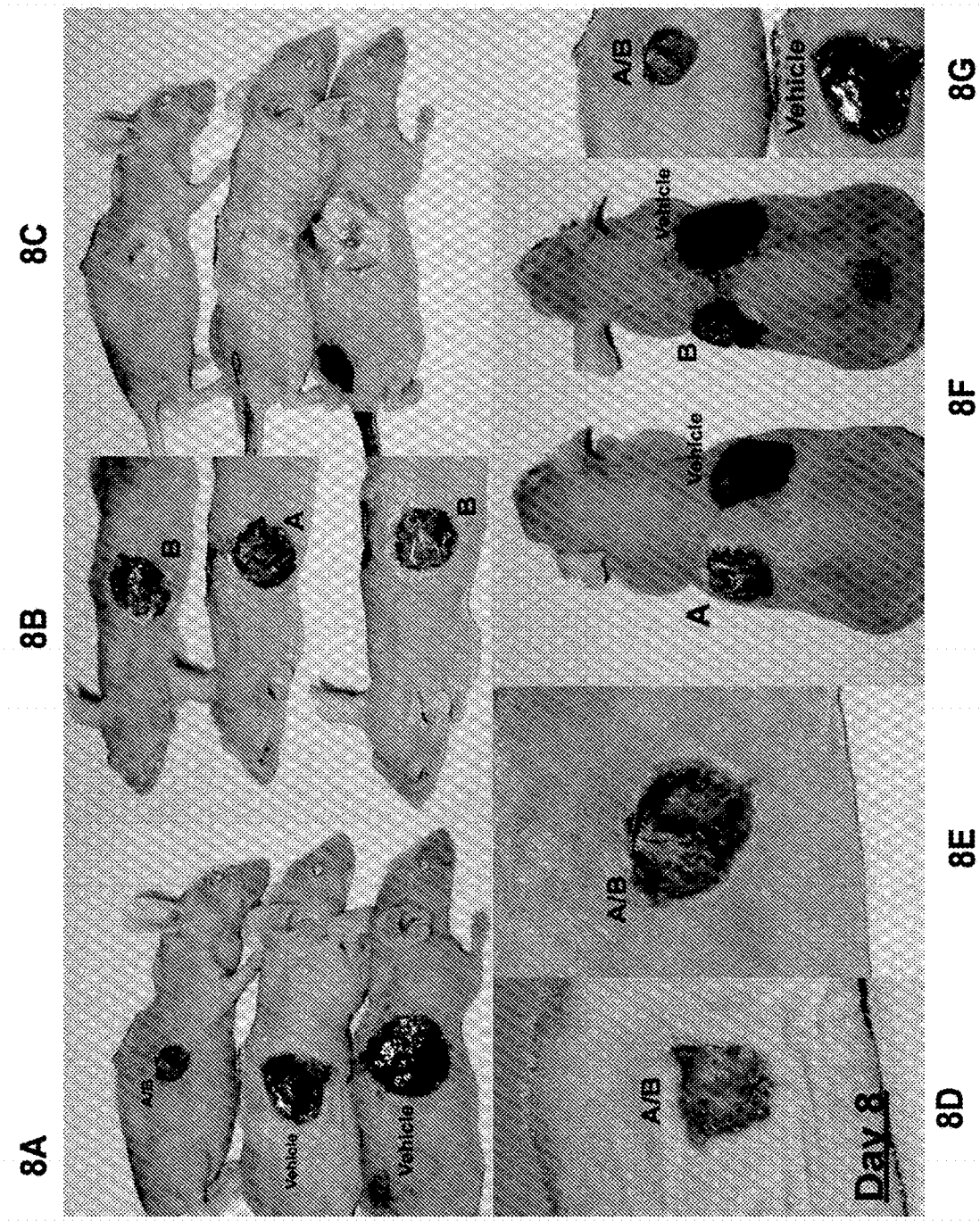

FIGS. 8A-G are pictures depicting CD1 nude diabetic mice on day 8 of the experiment. FIG. 8A shows three representative mice on day 8 of the experiment where the dorsal skin wounds have been treated with vehicle or with a cream containing both EPO and FN (marked A/B); FIG. 8B shows 3 representative mice on day 8 of the experiment where the dorsal skin wounds have been treated with a cream containing only EPO (marked A) or with a cream containing only FN (marked B); FIG. 8C shows 3 representative mice on day 8 of the experiment where the dorsal skin wounds have been treated with a cream containing only EPO (bottom mouse), a cream containing only FN (middle mouse) and a cream containing both EPO and FN (top mouse); FIG. 8D shows a wound on day 8 of the experiment treated with a cream containing both EPO and FN (marked A/B); FIG. 8E shows a wound on day 8 of the experiment treated with a cream containing both EPO and FN (marked A/B); FIG. 8F shows two representative mice on day 8 of the experiment where the dorsal skin wounds of each mouse was treated with a cream containing only EPO (marked A) or with a cream containing only FN (marked B) compared to treatment with vehicle; and FIG. 8G shows a comparison between wounds of two mice on day 8 of the experiment, one treated with a cream containing both EPO and FN (A/B) and the other treated with vehicle.

Figure 9:
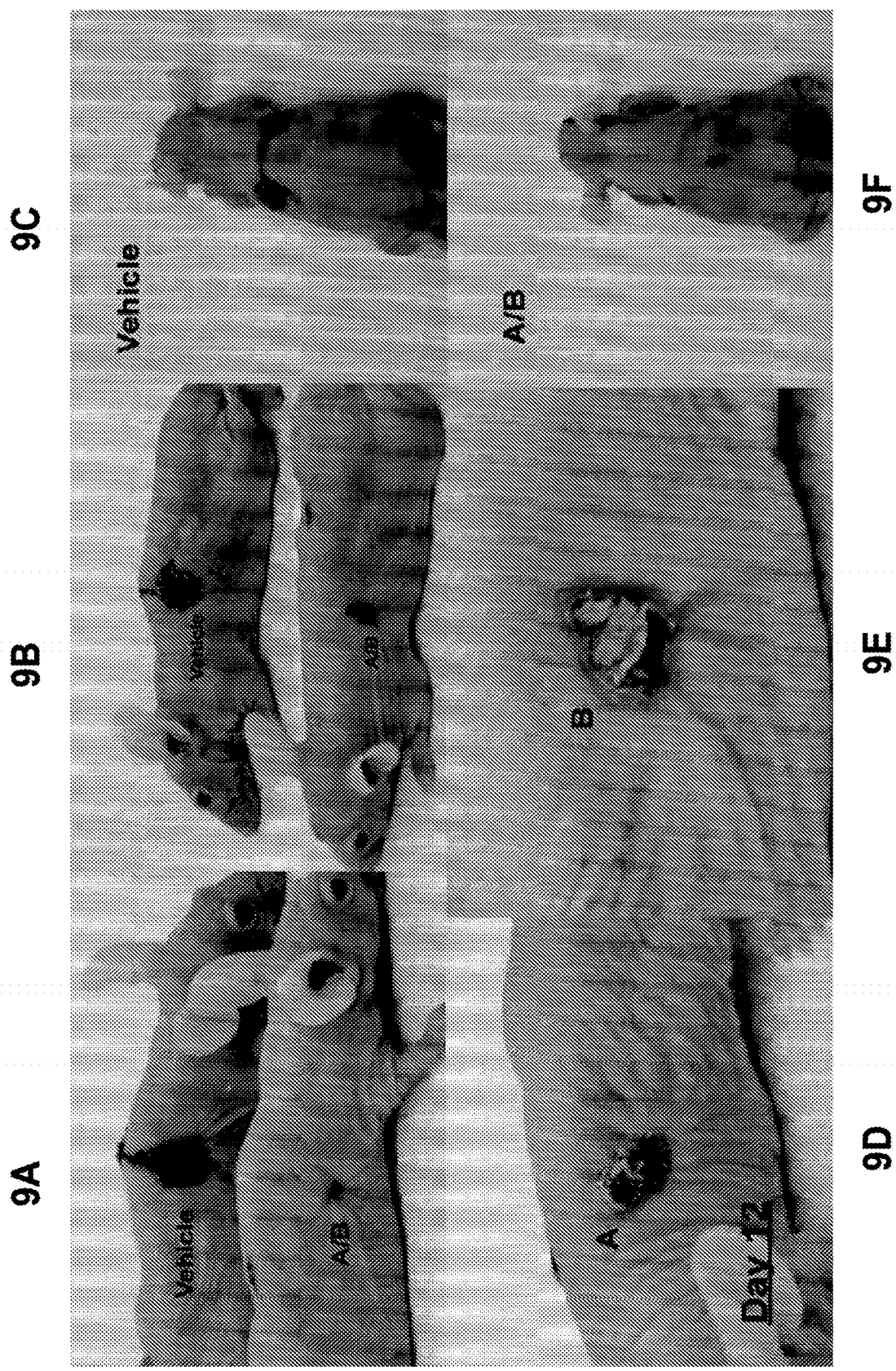

FIGS. 9A-F are pictures depicting CD1 nude diabetic mice on day 12 of the experiment. FIG. 9A shows a comparison between two representative mice on day 12 of the experiment where the dorsal skin wounds have been treated with vehicle or with a cream containing both EPO and FN (marked A/B); FIG. 9B shows a comparison between two representative mice on day 12 of the experiment where the dorsal skin wounds have been treated with vehicle or with a cream containing both EPO and FN (marked A/B); FIG. 9C shows a wound on day 12 of the experiment treated with a vehicle cream; FIG. 9D shows a wound on day 12 of the experiment treated with a cream containing only EPO (marked A); FIG. 9E shows a wound on day 12 of the experiment treated with a cream containing only FN (marked B); and FIG. 9F shows a wound on day 12 of the experiment treated with a cream containing both EPO and FN (marked A/B).

Figure 10:
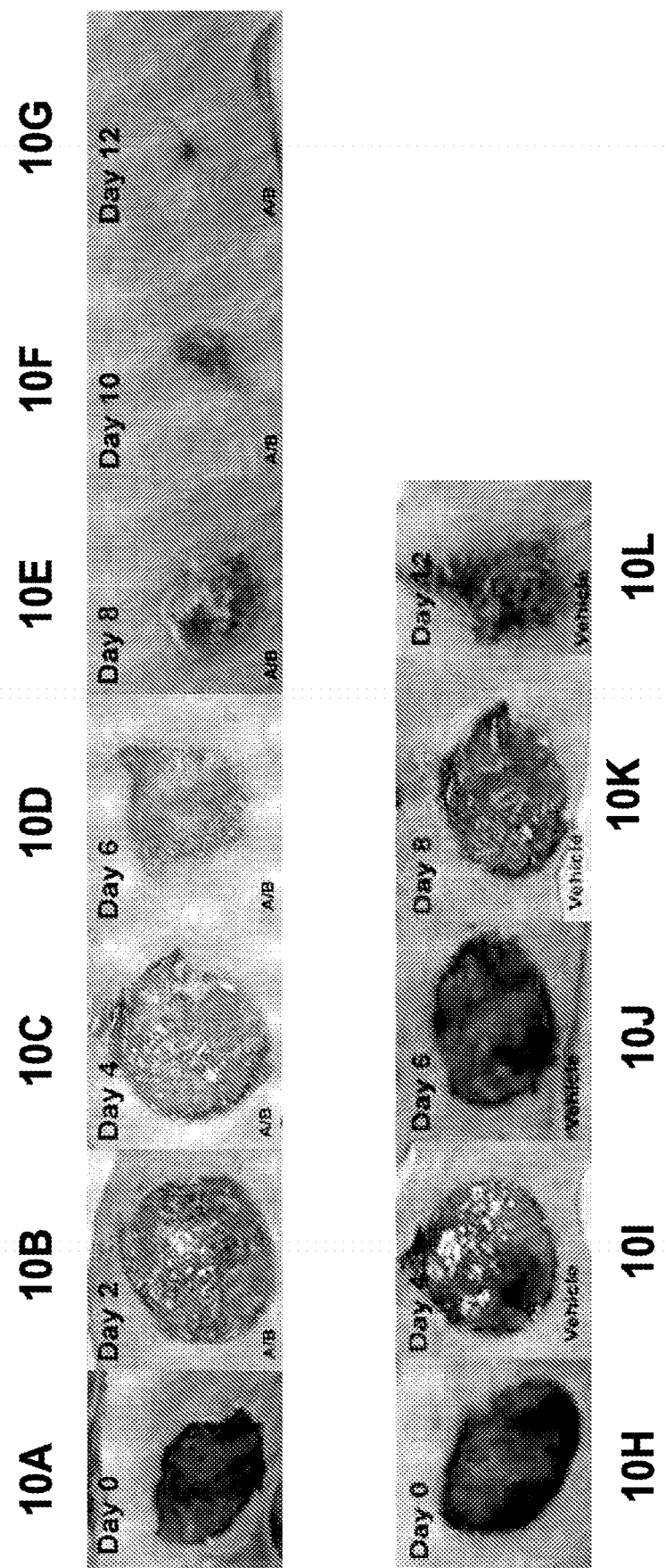
Figure 11:
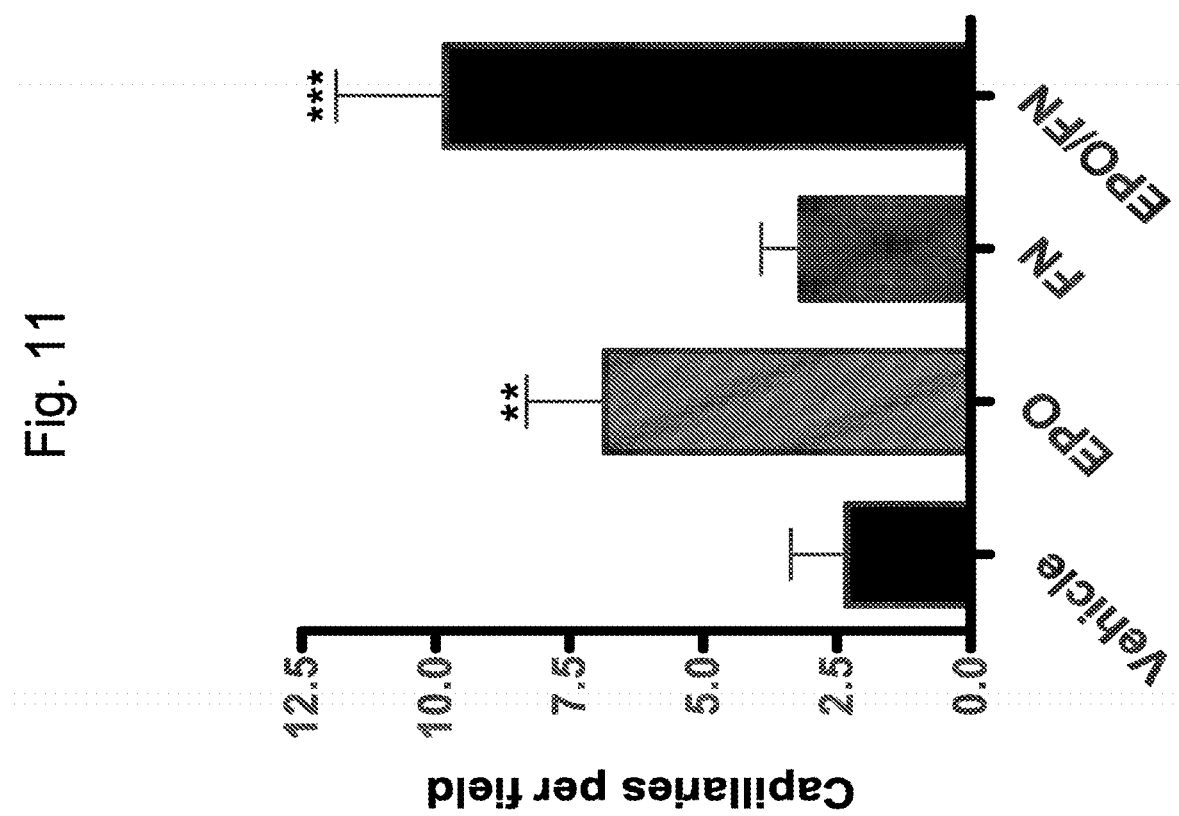

FIGS. 10A-L are pictures depicting wound closure in CD1 nude diabetic mice from day 1 to day 12 of treatment. FIG. 10A shows a wound treated with a cream containing both EPO and FN on day 0; FIG. 10B shows a wound treated with a cream containing both EPO and FN on day 2; FIG. 10C shows a wound treated with a cream containing both EPO and FN on day 4; FIG. 10D shows a wound treated with a cream containing both EPO and FN on day 6; FIG. 10E shows a wound treated with a cream containing both EPO and FN on day 8; FIG. 10F shows a wound treated with a cream containing both EPO and FN on day 10; FIG. 10G shows a wound treated with a cream containing both EPO and FN on day 12; FIG. 10H shows a wound treated with a vehicle cream on day 0; FIG. 10I shows a wound treated with a vehicle cream on day 4; FIG. 10J shows a wound treated with a vehicle cream on day 6; FIG. 10K shows a wound treated with a vehicle cream on day 8; and FIG. 10L shows a wound treated with a vehicle cream on day 12;

FIG. 11 is a bar graph depicting microvessel density (MVD) in wounds of diabetic mice at the end of treatment. The graph shows assessment of capillaries in tissue samples from wounds of mice treated with vehicle, with a cream containing only EPO, with a cream containing only FN or with a cream containing both EPO and FN using immunohistochemical staining of CD31.

Figure 12:
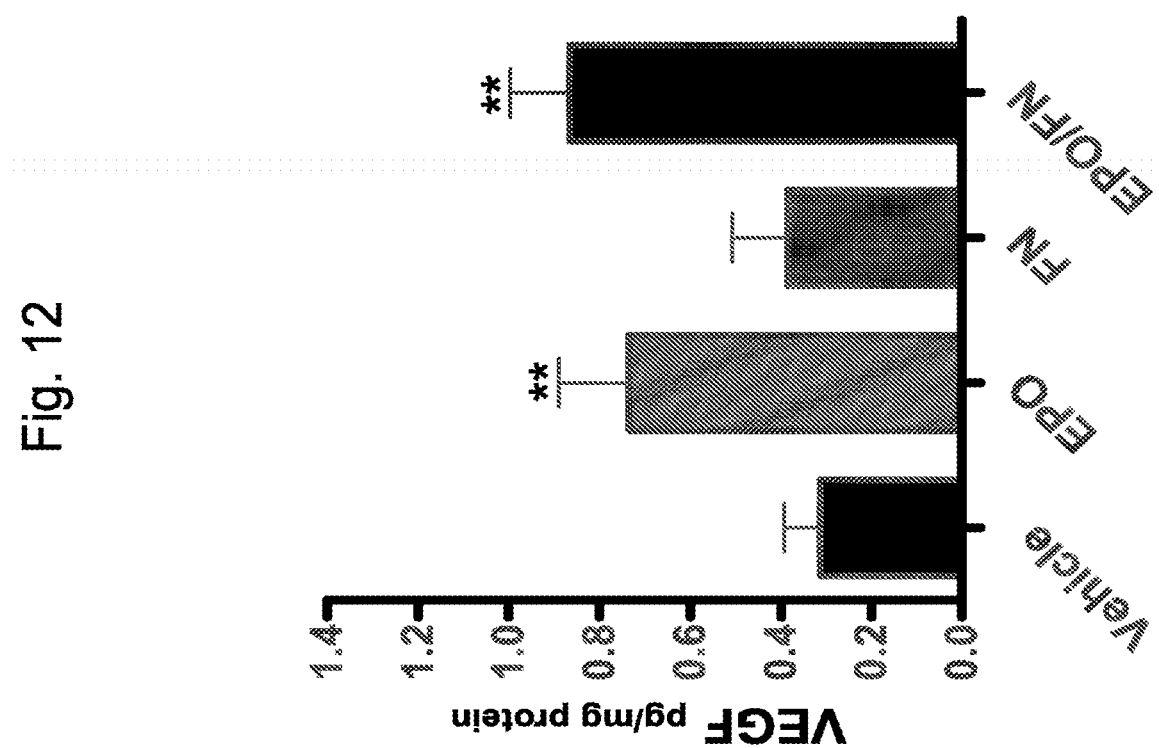

FIG. 12 is a bar graph depicting levels of the vascular endothelial growth factor (VEGF) in wounds of diabetic mice at the end of treatment. The graph shows VEGF content in tissue samples from wounds of mice treated with vehicle, with a cream containing only EPO, with a cream containing only FN or with a cream containing both EPO and FN.

Figure 13:
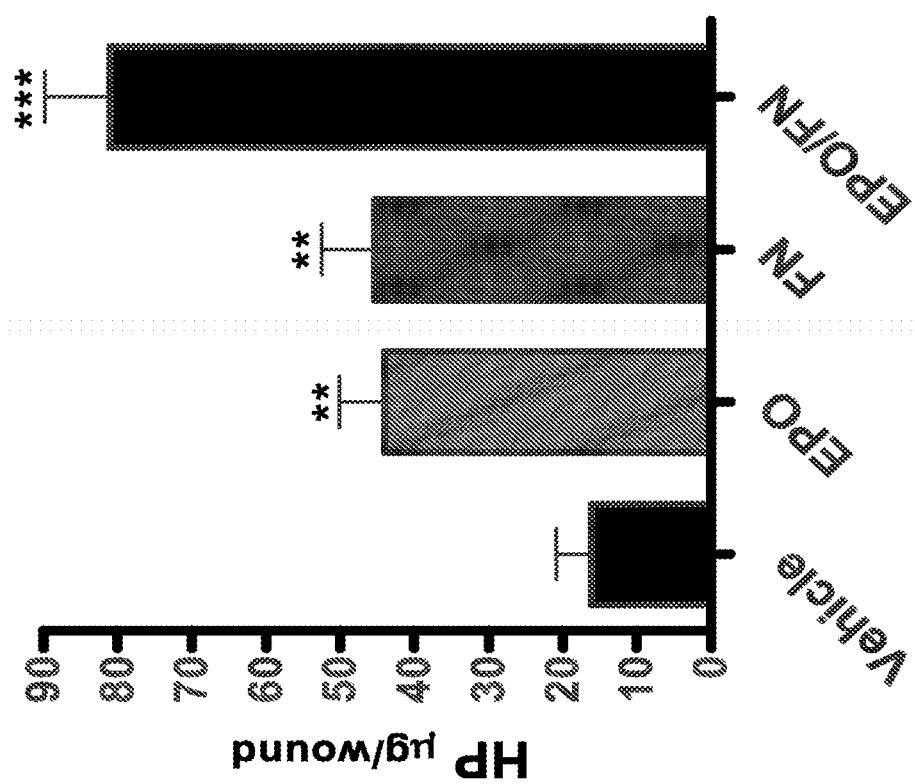

FIG. 13 is a bar graph depicting levels of Hydroxyproline (HP) in wounds of diabetic mice at the end of treatment. The graph shows HP content in tissue samples from wounds of mice treated with vehicle, with a cream containing only EPO, with a cream containing only FN or with a cream containing both EPO and FN.

FIGS. 14A-B depict β-1 integrin expression levels following in vitro stimuli of HEMCs with EPO. FIG. 14A shows primary human epidermal microvascular cells (HEMCs) treated with escalating doses of EPO (0.01, 0.1 and 1 μg/mL/day) for 3 consecutive days. At the end of day 3, HEMCs were tested for the β-1 integrin expression by western blot; and FIG. 14B shows a densitometer analysis of the western blot.

Figure 15B:
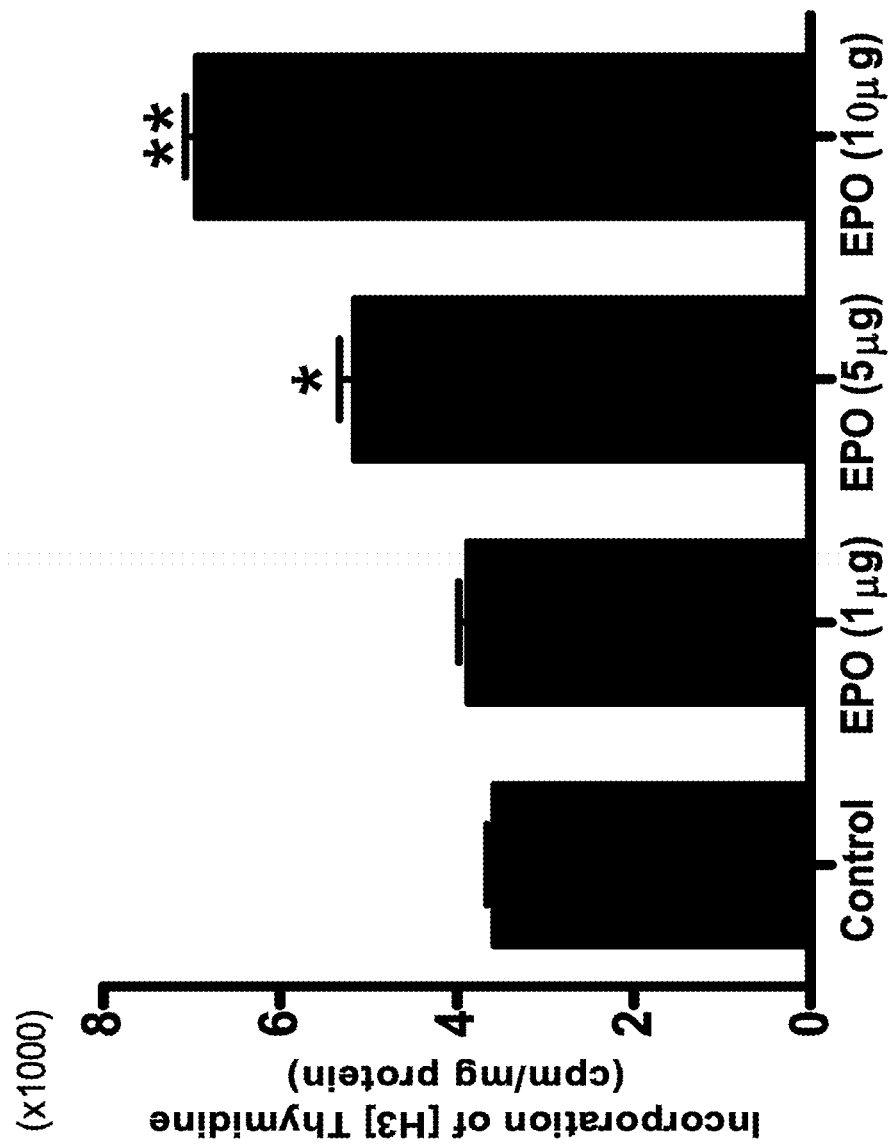

FIGS. 15A-B depict the effect of EPO with or without FN (as indicated) on cell proliferation. FIG. 15A depicts the effect of EPO on the proliferation of primary keratinocytes (KRCT); and FIG. 15B depicts the effect of EPO and FN on the proliferation of primary keratinocytes (fibronectin coated).

Figure 16A:
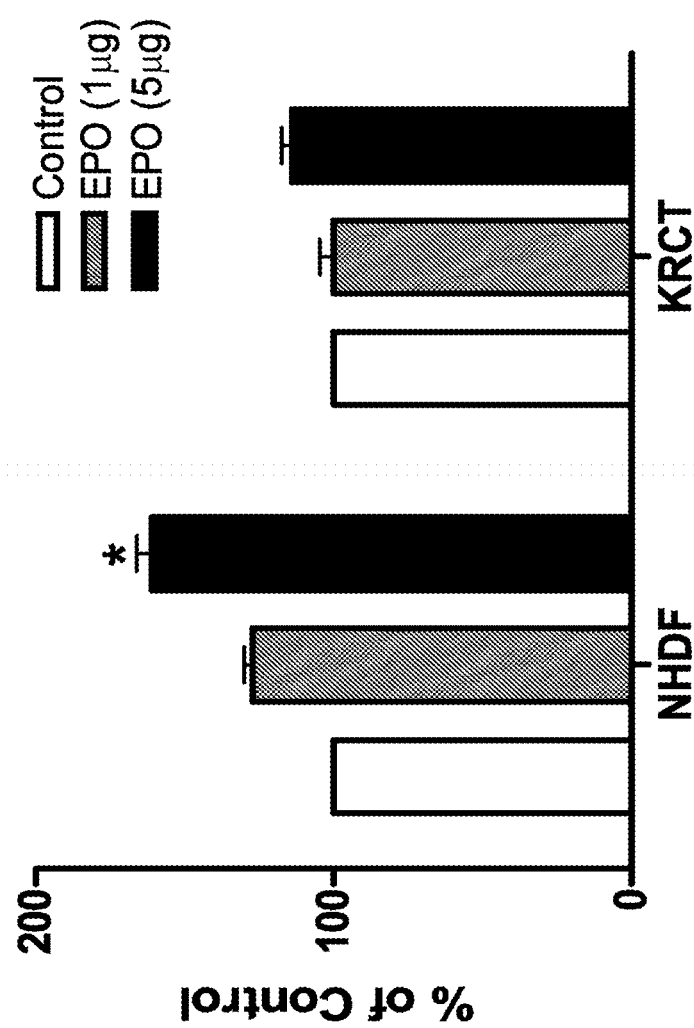

FIGS. 16A-B depict the effect of EPO with or without FN (as indicated) on SOD activity. FIG. 16A depicts the effect of EPO on SOD activity in primary human dermal fibroblasts (NHDF) and keratinocytes of adult skin (KRCT) (plates were not coated with FN); FIG. 16B depicts the effect of EPO and FN on SOD activity in NHDF and KRCT (plates were coated with FN).

Figure 17A:
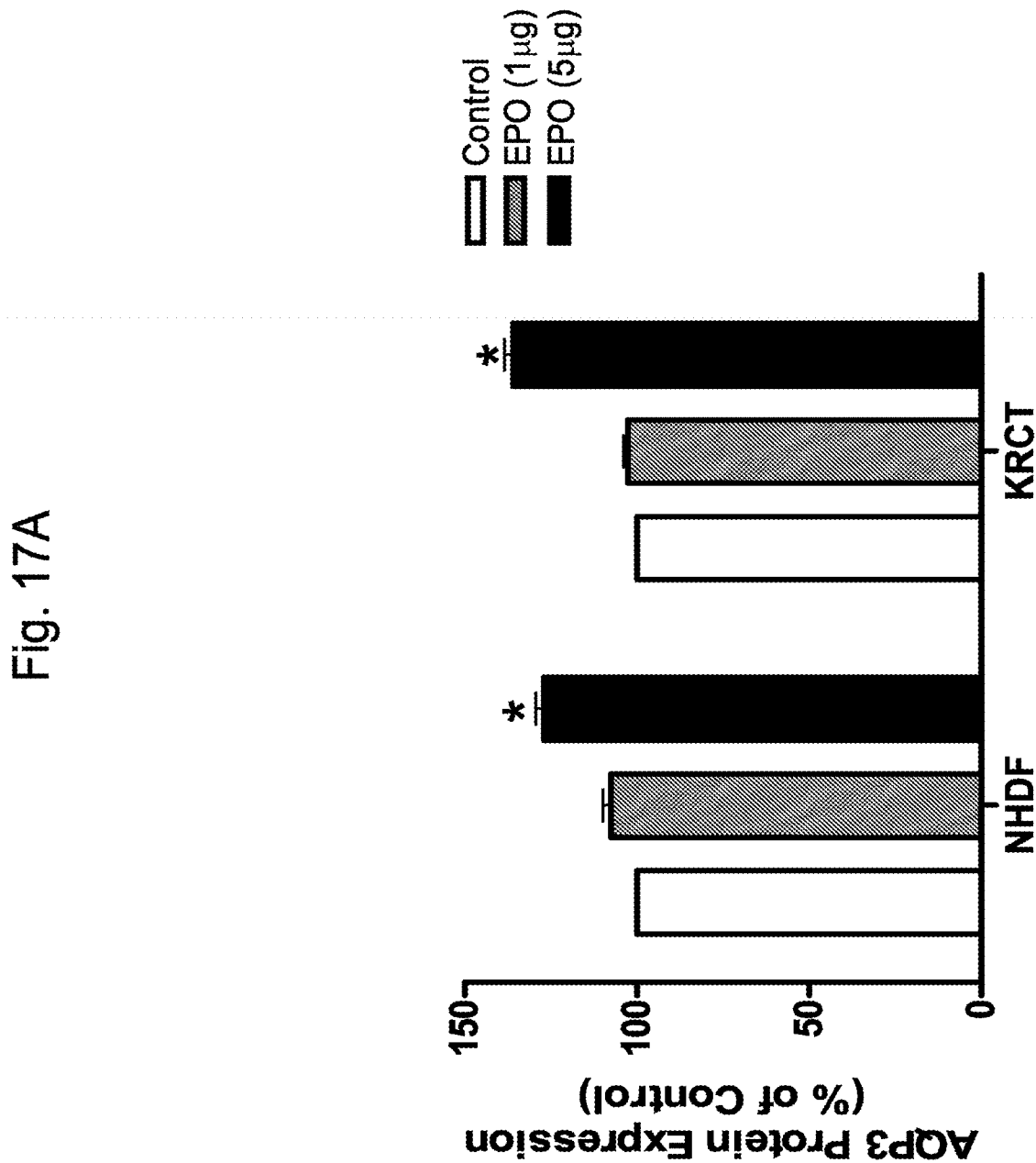
Figure 17B:
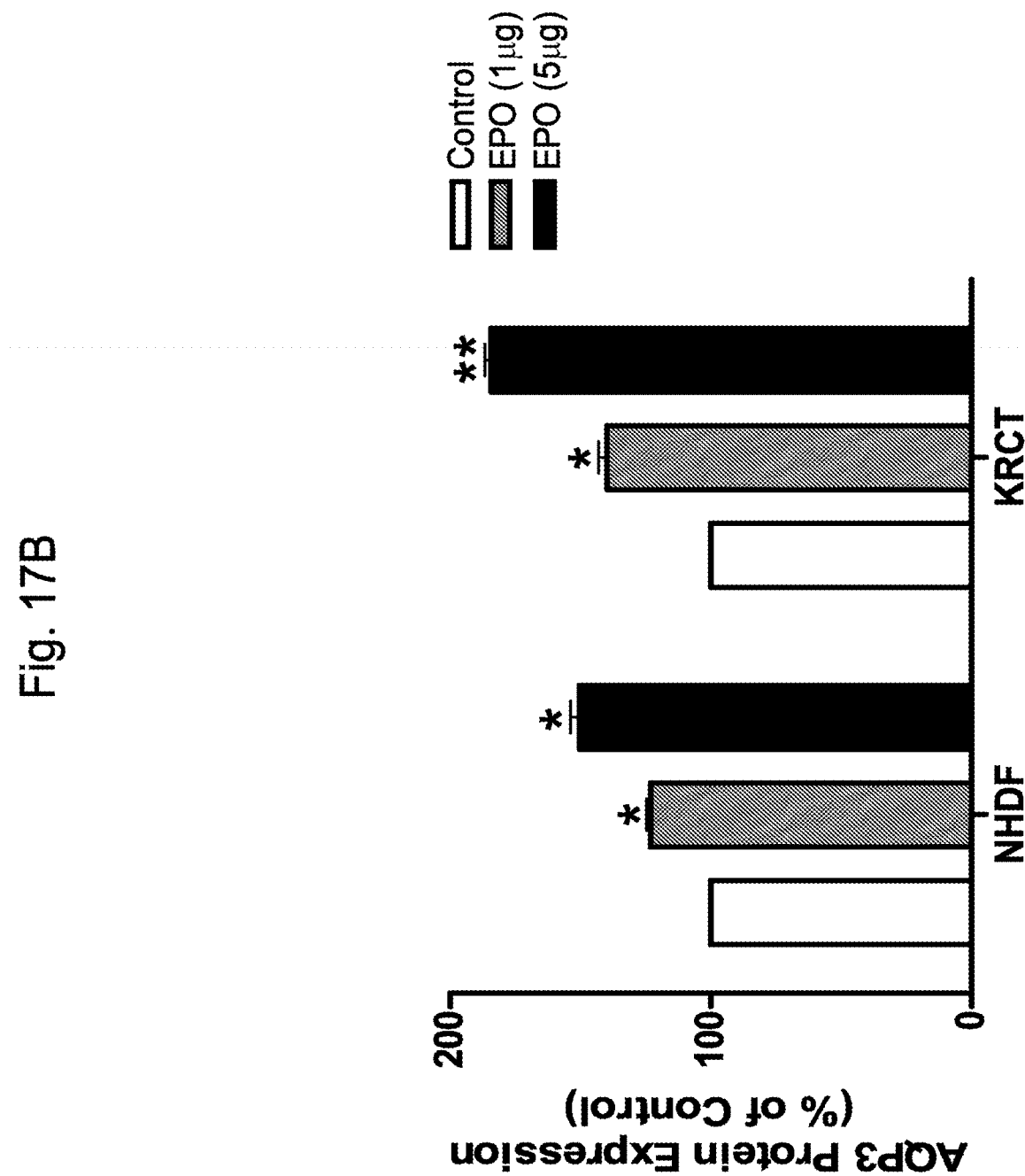

FIGS. 17A-B depict the effect of EPO with or without FN (as indicated) on Aquaporin-3 expression. FIG. 17A depicts the effect of EPO on AQP3 expression in NHDF and KRCT (plates were not coated with FN); FIG. 16B depicts the effect of EPO on AQP3 expression in NHDF and KRCT (plates were coated with FN).

FIGS. 18A-B depict the expression of the pro-apoptotic protein Bax and the anti-apoptotic protein Bcl-xL in wound tissues treated topically with creams containing vehicle, low EPO concentrations (5 μg/mL) and high EPO concentrations (25 μg/mL). Proteins from wounded tissues (40 μg/wound), obtained from six randomly chosen wounds from each group of rats, were loaded for western immunoblots. FIG. 18A depicts arbitrary units (mean±S.E.M.) of either Bax (black bars) or Bcl-xL (white bars) expression. Representative blots are shown; FIG. 18B depicts apoptosis sensitivity as determined by the ratio between mean expression of Bax and Bcl-xL; (Bax/Bcl-xL). Of note, * depicts $P<0.05$, ** depicts $P<0.001$; significant difference from the vehicle group.

DESCRIPTION OF EMBODIMENTS OF THE INVENTION

The present invention, in some embodiments thereof, relates to Erythropoietin and Fibronectin compositions and, more particularly, but not exclusively, to the use of same in therapeutic and cosmetic applications.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventor has uncovered that specific dosages of topically applied Erythropoietin (EPO) and Fibronectin (FN) significantly accelerate wound healing while promoting angiogenesis, inducing extracellular matrix production and reepithelialization. These findings suggest the use of the present teachings in promoting wound healing and connective tissue reconstruction.

As is shown hereinbelow and in the Examples section which follows, the present inventor has uncovered through laborious experimentation that certain concentrations of EPO and FN are desirable for wound healing and promoting collagen synthesis. The present inventor has specifically shown that EPO and FN act synergistically, probably (but not necessarily) through a β1-integrin pathway (see Example 3 hereinbelow) or erythropoietin receptor pathway, to promote angiogenesis, extracellular matrix (collagen) deposit and wound healing. Thus, the present invention envisions the use of these specific dosages of EPO and FN for wound healing, treatment of ischemia and promoting connective tissue reconstruction.

As is shown in FIGS. 1 and 6 and is described in Examples 1 and 2 of the Examples section which follows, topical application of a cream containing EPO or a cream containing FN significantly accelerated wound healing in diabetic rats and mice. Significant wound healing was recorded as early as 6 days after the beginning of treatment and complete wound closure was recorded 12 days after the beginning of EPO treatment in diabetic rats (see FIG. 1). However, topical application of a cream containing both EPO and FN significantly accelerated wound closure as early as 4 days after the beginning of treatment in diabetic mice and resulted in complete wound closure on day 8 of treatment (see FIG. 6 and FIGS. 10A-L). Furthermore, topical application of a cream containing EPO or a cream containing both EPO and FN significantly increased microvessel density (see FIGS. 2 and 11) and the levels of vascular endothelial growth factor (see FIGS. 3 and 12) in wounds of diabetic rats and mice, respectively. In addition, as is shown in FIGS. 4 and 13 and is described in Examples 1 and 2, topical application of a cream containing only EPO or a cream containing only FN resulted in an increase in connective tissue reconstruction (FIGS. 4 and 13). However, topical application of a cream containing both EPO and FN significantly accelerated connective tissue reconstruction (see FIG. 13), by 2 folds compared to treatment with a cream containing only EPO or only FN and by 5 folds compared to treatment with vehicle. Taken together, these results substantiate the value of EPO and FN at those dosages uncovered by the present study in angiogenesis, connective tissue reconstruction and in wound healing.

Thus, according to one aspect of the present invention there is provided a method of promoting wound healing and connective tissue reconstruction in a subject in need thereof.

The phrase "connective tissue" as used herein refers to animal tissue in which the extracellular matrix (ECM) and specifically collagen, forms the major part, which tissue functions to support and bind other body tissues and parts to one another. A typical example is the skin and internal organs.

The phrase "connective tissue reconstruction" as used herein refers to the restoration of aesthetics, structure, function, and physiology to the damaged or unhealthy tissue. This reconstruction leads to regenerative healing. Furthermore, connective tissue reconstruction refers to the increase in collagen production in the healthy tissue. In an exemplary embodiment, reconstruction leads to a halt in tissue deterioration. In other exemplary embodiments connective tissue reconstruction is devoid of fibrosis.

The phrase "damaged or unhealthy tissue" as used herein refers to a deviation from healthy functional tissue. In the case of skin, a skin that is weaker, less elastic, and is more prone to injury than healthy skin. The structure of unhealthy or damaged skin is inferior to that of healthy skin (for example, the dermis and epidermis contain fewer cells and collagen). One purpose for treating unhealthy skin is to reduce further deterioration of skin and restore its function to normal or near-normal level.

The phrase "healthy tissue" as used herein refers to skin that is strong, elastic, smooth and plump. One purpose of treating healthy skin is to prevent deterioration of skin induced by aging or environmental stress including excessive sunlight and microbial infection.

The term "promoting" in respect to a connective tissue refers to the process of increasing the production of collagen by skin cells such as fibroblasts and keratinocytes, in a manner that allows tissue regeneration. Thus in some embodiments of the present invention, promoting refers to at least about 10%, 20%, 50%, 80% increase in tissue regeneration or at least about 10%, 20%, 50%, 80% arrest in tissue degradation. Those of skill in the art will understand that various methodologies and assays can be used to assess the promotion of tissue regeneration, and similarly, various methodologies and assays may be used to assess the arrest of tissue degradation.

Compositions of some embodiments of the present invention are envisioned to promote connective tissue reconstruction in many skin conditions and maladies including, but not limited to, aging skin, skin exposed to excessive sunlight (e.g. photoaged or photo damaged skin), age spots, unwanted wrinkles, fine lines, appearance of aged skin (e.g. sags, changes in tone and texture), blemish, stressed skin, rough skin, dry skin, cellulitis, irritated skin, scars, saggy lips, acne, actinic keratoses.

The term "wound" as used herein refers broadly to injuries to the skin and subcutaneous tissue as well as internal organs initiated in any one of a variety of ways (e.g., pressure sores from extended bed rest, wounds induced by trauma, wounds received during or following a surgical procedure and the like) and with varying characteristics. Exemplary examples include, but are not limited to, bruises, scrapes, burn wounds, sunburn wounds, incisional wounds, excisional wounds, surgical wounds, necrotizing fasciitis, ulcers, venous stasis ulcers, diabetic ulcers, decubitus ulcers, aphthous ulcers, pressure ulcers, scars, alopecia areata, dermatitis, allergic contact dermatitis, atopic dermatitis, berloque dermatitis, diaper dermatitis, dyshidrotic dermatitis, psoriasis, eczema, erythema, warts, anal warts, angioma, cherry angioma, athlete's foot, atypical moles, basal cell carcinoma, Bateman's purpura, bullous pemphigoid, candida, chondrodermatitis helicis, Clark's nevus, cold sores, condylomata, cysts, Darier's disease, dermatofibroma, Discoid Lupus Erythematosus, nummular eczema, atopic eczema, dyshidrotic eczema, hand eczema, Multiforme Erythema Nodosum, Fordyce's Condition, Folliculitis Keloidalis Nuchae, Folliculitis, Granuloma Annulare, Grover's Disease, heat rash, herpes simplex, herpes zoster (shingles), Hidradenitis Suppurativa, Hives, Hyperhidrosis, Ichthyosis, Impetigo, Keratosis Pilaris, Keloids, Keratoacanthoma, Lichen Planus, Lichen Planus Like Keratosis, Lichen Simplex Chronicus, Lichen Sclerosus, Lymphomatoid Papulosis, Lupus of the Skin, Lyme Disease, Lichen Striatus, Myxoid Cysts, Mycosis Fungoides, Molluscum Contagiosum, Moles, Nail Fungus, Necrobiosis Lipoidica Diabeticorum, Nummular Dermatitis, Onychoschizia, Onychomycosis, Pityriasis Lichenoides, Pityriasis Rosea, Pityriasis Rubra Pilaris, Plantar Warts, Poison Ivy, Poison Oak, Pompholyx, Pseudofolliculitis Barbae, Pruritus Ani and Pityriasis Alba.

Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" used herein refers to wounds that encompass Grades I-III; examples of partial thickness wounds include burn wounds, pressure sores, venous stasis ulcers, and diabetic ulcers.

The term "deep wound" used herein is meant to include both Grade III and Grade IV wounds.

The term "chronic wound" used herein refers to a wound that has not healed within thirty days.

The term "healing" in respect to a wound refers to the process of repairing a wound such as by scar formation (in exemplary embodiments healing is devoid of fibrotic tissue formation).

In a specific embodiment, compositions of some embodiments of the present invention promote i.e., accelerate the healing process.

The phrase "inducing or accelerating a healing process of a skin wound" refers to either the induction of the formation of granulation tissue of wound contraction and/or the induction of epithelialization (i.e., the generation of new cells in the epithelium). Wound healing is conveniently measured by decreasing wound area.

The present invention contemplates treating all wound types, including deep wounds and chronic wounds.

It will be appreciated that the present inventor has also uncovered that the mentioned compositions can be used for treating ischemia such as by promoting angiogenesis in a wounded tissue.

As used herein the term "ischemia" refers to localized tissue anemia due to at least partial obstruction of the inflow of arterial blood. Exemplary examples of ischemia-related tissue damage include damage and death of skin tissue (e.g. wound) as a result of reduced or interrupted blood flow to the tissue.

As used herein the term "treating" refers to preventing, curing, reversing, attenuating, alleviating, minimizing, suppressing or halting the deleterious effects of an ischemic condition, such as by enhancing perfusion. Those of skill in the art will understand that various methodologies and assays can be used to assess the development of a condition, and similarly, various methodologies and assays may be used to assess the reduction, remission or regression of the condition.

Treatment can be evaluated by routine experimentation, such as the models described in the Examples section below. Outcome measures such as perfusion and survival, as well as histological and functional criteria, can be employed to assess the efficacy of varying the different parameters, in order to approach optimal efficiency in numbers of cells having maximal therapeutic value in treating an ischemic condition. Additional parameters known in the art that can be quantified for determining perfusion in an affected tissue are angiography and MRI, and clinical parameters such as extent of tissue necrosis in the affected area, tissue ulceration in the ischemic area, and amputation of digits and/or limbs.

In the context of wound healing "promoting" refers to the ability to permit or assist wound healing, in a manner that allows treatment thereof. Thus in some embodiments of the present invention, promoting refers to at least about 10%, 20%, 50%, 80% reduction in time taken to achieve healing or at least about 10%, 20%, 50%, 80% increase in wound closure.

As used herein the term "subject" refers to any mammal, (e.g., a human being or domesticated animals), male or female at any age that experiences or may experience tissue damage or suffers from a wound or from ischemia, at any stage and/or degree.

As mentioned, the method according to this aspect of the present invention is achieved by topically administering to the subject the indicated dosages of EPO and FN.

As used herein the term "Erythropoietin" refers to a mammalian (e.g., human) Erythropoietin protein (interchangeably used with polypeptide) or mimetics thereof such as set forth in GenBank Accession No. NP_000790. Erythropoietin may be synthesized using recombinant DNA techniques or solid phase technology. Erythropoietin is also commercially available (e.g., Cytolab/Peprotech, Rehovot, Israel; Arenesp, Amgen, Thousand Oaks, Calif., USA; and Epogen, Amgen, Thousand Oaks, Calif., USA, Bristol-Myers Squibb, Roche and Sanofi-Aventis). Erythropoietin may be used as an entire glycoprotein or as only a protein subunit devoid of the bound sugar. Since the Erythropoietin of the present invention is used for clinical applications, it is preferably sterile or may be purified of possible contaminating factors (e.g., bacteria or bacterial components, such as by filter).

As used herein the term "Fibronectin" refers to a mammalian (e.g., human) Fibronectin protein (interchangeably used with polypeptide) or mimetics thereof such as set forth in GenBank Accession No. NP_002017. Fibronectin may be synthesized using recombinant DNA techniques or solid phase technology. Fibronectin is also commercially available (e.g., Chemicon International Inc., Temecula, Calif., USA). Since the Fibronectin of the present invention is used for clinical applications, it is preferably sterile or may be purified of possible contaminating factors (e.g., bacteria or bacterial components, such as by filter).

It will be appreciated that when mimetics compositions are used the dosages of FN and EPO should be calibrated such as according to the molar value. Such a calibration is a routine calculation for those of ordinary skill in the art.

Pharmaceutical or cosmetic compositions of the present invention may comprise Erythropoietin and Fibronectin in a co-formulation (such as provided in Example 2 further below) or in two separate compositions.

As used herein the phrase "topically administering" refers to applying or spreading the compositions of the present invention onto the surface of the body, i.e. skin, scalp, hair, nails and the like, preferably on the surface of the damaged tissue (e.g., skin), wound or on the surface of an ischemic tissue. When not co-formulated, administration of Erythropoietin and Fibronectin may be effected concomitantly or sequentially.

It will be appreciated that the dose of Erythropoietin and Fibronectin applied according to the teachings of the present invention may vary. Thus, Erythropoietin can be administered at a dose between 10-30 µg per $cm^2$ tissue depending on the severity of the tissue damage or wound to be treated. In one embodiment the dose of Erythropoietin is between 15-25 µg per $cm^2$ tissue. In another embodiment the dose of Erythropoietin is about 20 µg per $cm^2$ tissue. Fibronectin can be administered at a dose between 100-300 µg per $cm^2$ tissue depending on the severity of the tissue damage or wound to be treated. In one embodiment the dose of Fibronectin is between 150-250 µg per $cm^2$ tissue. In another embodiment the dose of Fibronectin is about 200 µg per $cm^2$ tissue.

Likewise, for the treatment of ischemia, the dose of Erythropoietin and Fibronectin may vary. Erythropoietin can be administered at a dose between 10-30 µg per $cm^2$ tissue depending on the severity of ischemia to be treated. In one embodiment the dose of Erythropoietin is between 15-25 µg per $cm^2$ tissue. In another embodiment the dose of Erythropoietin is about 20 µg per $cm^2$ tissue. Fibronectin can be administered at a dose between 100-300 µg per $cm^2$ tissue depending on the severity of ischemia to be treated. In one embodiment the dose of Fibronectin is between 150-250 µg per $cm^2$ tissue. In another embodiment the dose of Fibronectin is about 200 µg per $cm^2$ tissue.

The compositions including Erythropoietin and/or Fibronectin of the present invention can be administered to the subject per se or in a pharmaceutical or cosmetic composition.

As used herein a "pharmaceutical or cosmetic composition" refers to a preparation of the active ingredients described herein with other chemical components such as physiologically suitable carriers and excipients. The purpose of the composition is to facilitate administration of the active ingredients (e.g., EPO and FN) to the subject.

As used herein the term "active ingredient" refers to the Erythropoietin and Fibronectin compositions accountable for the intended biological effect (i.e., promoting wound healing, connective tissue reconstruction and treating ischemia).

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the composition (pharmaceutical composition or cosmetic composition) to further facilitate administration of an active ingredient of the present invention.

Techniques for formulation and administration of drugs may be found in "Remington's Pharmaceutical Sciences," Mack Publishing Co., Easton, Pa., latest edition, which is incorporated herein by reference.

The composition may be formulated as a unit dosage form. In such form, the preparation is subdivided into unit doses containing appropriate quantities of the active ingredients such as for a single administration. The unit dosage form can be a packaged preparation, the package containing discrete quantities of preparation, for example, an adhesive bandage, a non-adhesive bandage, a wipe, a baby wipe, a gauze, a pad and a sanitary pad.

The unit dosage form according to the teachings of the present invention may comprise Erythropoietin at a dose of about 10-30 µg, Fibronectin at a dose of about 100-300 µg, or both Erythropoietin at a dose of about 10-30 µg and Fibronectin at a dose of about 100-300 µg. In one embodiment, the unit dosage form comprise Erythropoietin at a dose of about 15-25 µg, Fibronectin at a dose of about 150-250 µg, or both Erythropoietin at a dose of about 15-25 µs and Fibronectin at a dose of about 150-250 µg. In another embodiment, the unit dosage form comprise Erythropoietin at a dose of about 20 µg, Fibronectin at a dose of about 200

μg, or both Erythropoietin at a dose of about 20 μg and Fibronectin at a dose of about 200 μg.

The quantity of active compound in a unit dose of preparation may be varied or adjusted according to the particular application.

The compositions (e.g., pharmaceutical or cosmetic compositions) of the present invention may be applied in a local manner, for example, via administration of the compositions directly onto a tissue region (e.g. wound) of a patient. Suitable routes of administration of the compositions may, for example, include topical (e.g., to a keratinous tissue, such as the skin, hair, nail, scalp) and mucosal (e.g., oral, vaginal, eye) administrations.

The compositions of the present invention may also be applied via injecting the composition including the active ingredient (e.g., EPO and FN) and a physiologically acceptable carrier. For local administration, the compositions may be injected into the wound, and/or into healthy skin that surrounds the wounded skin, or both.

Compositions of the present invention may be manufactured by processes well known in the art, e.g., by means of conventional mixing, dissolving, granulating, dragee-making, levigating, emulsifying, encapsulating, entrapping or lyophilizing processes.

The active ingredient may also be in a powder form for constitution with a suitable vehicle, e.g., sterile, pyrogen-free water based solution, before use.

Compositions for use in accordance with the present invention thus may be formulated in conventional manner using one or more physiologically acceptable carriers comprising excipients and auxiliaries, which facilitate processing of the active ingredients into preparations. Proper formulation is dependent upon the administration approach chosen.

Determination of a therapeutically effective amount is well within the capability of those skilled in the art, especially in light of the detailed disclosure provided herein.

For any preparation used in the method of the invention, the (therapeutically) effective amount or dose can be estimated initially from in vitro assays. In addition, a dose can be formulated in tissue cultures systems or in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity of the condition (e.g., the area, depth and degree of the tissue damage, wound or the ischemia) and the responsiveness of the tissue, dosing can be of a single or a plurality of administrations, with course of treatment lasting from several days to several weeks or until cure is effected or diminution of the skin condition is achieved. Preferably, the compositions of the present invention are administered at least once a day.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

Since the compositions of the present invention are utilized in vivo, the compositions are preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

Additional factors may be incorporated into the compositions of the present invention (i.e., Erythropoietin and Fibronectin described hereinabove). These include, but are not limited to, extracellular matrix components (e.g. vitronectin, laminin, collagen, elastin), growth factors (e.g. FGF 1, FGF 2, IGF 1, IGF 2, PDGF, EGF, KGF, HGF, VEGF, SDF-1, GM-CSF, CSF, G-CSF, TGF alpha, TGF beta, NGF and ECGF), hypoxia inducible factors (e.g. HIF-1 alpha and beta and HIF-2), hormones (e.g., insulin, growth hormone (GH), CRH, Leptin, Prolactin and TSH), angiogenic factors (e.g., angiogenin and angiopoietin), coagulation and anticoagulation factors [e.g., Factor I, Factor XIII, tissue factor, calcium, vWF, protein C, protein S, protein Z, fibronectin, antithrombin, heparin, plasminogen, low molecular weight heparin (Clixan), high molecular weight kininogen (HMWK), prekallikrein, plasminogen activator inhibitor-1 (PAI1), plasminogen activator inhibitor-2 (PAI2), urokinase, thrombomoduline, tissue plasminogen activator (tPA), alpha 2-antiplasmin and Protein Z-related protease inhibitor (ZPI)], cytokines (IL-1 alpha, IL-1 beta, IL-2, IL-3, IL-4, IL-5, IL-6, IL-7, IL-8, IL-9, IL-10, IL-11, IL-12, IL-13 and INF-alpha, INF, beta, and INF-gamma), chemokines (e.g., MCP-1 or CCL2), enzymes (e.g. endoglycosidases, exoglycosidases, endonucleases, exonucleases, peptidases, lipases, oxidases, decarboxylases, hydrases, chondroitinase, chondroitinase ABC, chondroitinase AC, hyaluronidase, keratanase, heparanases, heparanase splice variance, collagenase, trypsin, catalases), neurotransmitters (e.g., acetylcholine and monoamines), neuropeptides (e.g. substance P), vitamins (e.g., D-biotin, Choline Chloride, Folic acid, Myo-inositol, Niacinamide, D-Pantothenic acid, Calcium salts, Pyridoxal.HCl, Pyrodixine.HCl, Riboflavin, Thiamine.HCl, Vitamin B 12, vitamin E, vitamin C, vitamin D, vitamin B 1-6, vitamin K, vitamin A and vitamin PP), carbohydrates (e.g. Mono/Di/Polysaccharides including glucose, mannose, maltose and fructose), ions, chelators (e.g. Fe chelators, Ca chelators), antioxidants (e.g., Vitamin E, Quarcetin, superoxide scavengers, Superoxide dismutase), H2O2 scavengers, free radicals scavengers, Fe scavengers), fatty acids (e.g., Triglycerides, Phospholipids, Cholesterols, free fatty acids and non free fatty acids, fatty alcohol, Linoleic acid, oleic acid and lipoic acid), antibiotics (e.g., Penicillins, Cephalosporins and Tetracyclines), analgesics, anesthetics, antibacterial agents, anti-yeast agents, anti-fungal agents, antiviral agents, pro-biotic agents, anti-protozal agents, anti-pruritic agents, anti-dermatitis agents, anti-emetics, anti-inflammatory agents, anti-hyperkeratolyic agents, antiperspirants, anti-psoriatic agents, anti-seborrheic agents, antihistamine agents, amino acids (e.g., essential and non essential (from A-Z) especially glutamine and arginine), salts (e.g., prurivat salts and sulfate salts), sulfates (e.g. Calcium Sulfate), steroids (e.g., androgens, estrogens, progestagens, glucocorticoids and mineralocorticoids), catecholamines (e.g., Epinephrine and Nor-epinephrine), Nucleosides and Nucleotides (e.g., Purins and Pyrimidines), Prostaglandins (e.g. Prostaglandin E2), Leucotriens, Erythropoietins (e.g. Thrombopoietin), Proteoglycans (e.g. Heparan sulfate, keratan sulfate), Hydroxyapatites [e.g. Hydroxyapatite $(Ca_{10}(PO_4)_6(OH)_2)$], Haptoglobins (Hp1-1, Hp2-2 and Hp1-2), Superoxide dismutases (e.g. SOD 1/2/3), Nitric Oxides, Nitric Oxide donors (e.g. nitroprusside, Sigma Aldrich, St. Louis, Mo., USA, Glutathione peroxidases, Hydrating compounds (e.g. vasopressin), cells (e.g. Platelets), cell medium (e.g. M199, DMEM/F12, RPMI, Iscovs), serum (e.g. human serum, fetal calf serum, fetal bovine serum), buffers (e.g., HEPES, Sodium Bicarbonate), detergents (e.g., Tween), disinfectants, herbs, fruit extracts, vegetable extracts (e.g. cabbage, cucumber), flower extracts, plant extracts, flavinoids (e.g. pomegranate juice), spices, leafs (e.g. Green tea, Chamomile), Polyphenols (e.g. Red Wine), honey, lectins, microparticles, nanoparticles (lyposomes), micelles, calcium carbonate (CaCO3, e.g. precipitated calcium carbonate, ground/pulverized calcium carbonate, albacar, PCC, GCC), calcite, limestone, crushed marble, ground limestone, lime, chalk (e.g. whiting chalk, champagne chalk, french chalk) and co factors such as BH4 (tetrahydrobiobterine).

The present composition may also contain ingredients, substances, elements and materials containing, hydrogen, alkyl groups, aryl groups, halo groups, hydroxy groups, alkoxy groups, alkylamino groups, dialkylamino groups, acyl groups, carboxyl groups, carboamido groups, sulfonamide groups, aminoacyl groups, amide groups, amine groups, nitro groups, organo selenium compounds, hydrocarbons, and cyclic hydrocarbons.

The present composition may be combined with substances such as benzol peroxide, vasoconstrictors, vasodilatators, salicylic acid, retinoic acid, azelaic acid, lactic acid, glycolic acid, pyreuric acid, tannins, benzlidenecamphor and derivatives thereof, alpha hydroxyis, surfactants.

Compositions of some embodiments of the present invention may be bioconjugated to polyethylenglycol (e.g. PEG, SE-PEG) which preserves the stability (e.g., against protease activities) and/or solubility (e.g., within a biological fluid such as blood, digestive fluid) of the active ingredients (i.e. EPO and/or FN compositions of the present invention) while preserving their biological activity and prolonging its half-life.

In addition to the pharmaceutically effective amount of an agent disclosed herein, the compositions of this aspect of the present invention also include a dermatologically acceptable carrier.

The phrase "dermatologically acceptable carrier", refers to a carrier which is suitable for topical application onto the skin, i.e., keratinous tissue, has good aesthetic properties, is compatible with the active agents of the present invention and any other components, and is safe and non-toxic for use in mammals.

In order to enhance the percutaneous absorption of the active ingredients (e.g., Erythropoietin and/or Fibronectin of the present invention), one or more of a number of agents can be added to the compositions including, but not limited to, dimethylsulfoxide, dimethylacetamide, dimethylformamide, surfactants, azone, alcohol, acetone, propylene glycol and polyethylene glycol.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion, a soap, a paste, an emulsion, a gel, a spray or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Examples of suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986), each of which is fully incorporated by reference in its entirety.

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form.

Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991 each of which is fully incorporated by reference in its entirety. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant.

A wide variety of anionic surfactants are also useful herein. See, e.g., U.S. Pat. No. 3,929,678, to Laughlin et al., issued Dec. 30, 1975 which is fully incorporated by reference in its entirety. In addition, amphoteric and zwitterionic surfactants are also useful herein.

The compositions of the present invention can be formulated in any of a variety of forms utilized by the pharmaceutical industry for skin application including solutions, lotions, sprays, creams, ointments, salves, gels, oils, wash, etc., as described below.

In addition, compositions of the present invention can be used as a supplement in a variety of cosmetics. Cosmetics are substances used to enhance or protect the appearance or odor of the human body. Examples of cosmetics include skin-care creams, lotions, powders, perfumes, lipsticks, fingernail and toe nail polish, eye and facial makeup, perfumes, aftershaves, manicures, permanent waves, shaving foams and creams, hair colors, hair sprays and gels, deodorants, baby products, bath oils, bubble baths, bath salts, butters and many other types of products.

The compositions of the present invention may be formulated viscous enough to remain on the treated skin area, does not readily evaporate, and/or is not easily removed by rinsing with water, but rather is removable with the aid of soaps, cleansers and/or shampoos.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

The topical compositions of the subject invention, including but not limited to lotions and creams, may comprise a dermatologically acceptable emollient. As used herein, "emollient" refers to a material useful for the prevention or relief of dryness, as well as for the protection of the skin. Wide varieties of suitable emollients are known and may be used herein. See, e.g., Sagarin, Cosmetics, Science and Technology, 2nd Edition, Vol. 1, pp. 3243 (1972), which contains numerous examples of materials suitable as an emollient and is fully incorporated herein by reference. A preferred emollient is glycerin.

Lotions and creams according to the present invention generally comprise a solution carrier system and one or more emollients.

The topically applied composition of the present invention may also include additional components which are added, for example, in order to enrich the compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention.

Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

The compositions of the present invention can be applied directly to the skin. Alternatively, it can be delivered via normal skin application by various transdermal drug delivery systems which are known in the art, such as transdermal patches that release the composition into the skin in a time released manner. Other drug delivery systems known in the arts include pressurized aerosol bottle, iontophoresis or sonophoresis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically mediated transport of therapeutic agents across the skin. Alternatively, or in addition, liposomes or micelles may also be employed as a delivery vehicle.

Since wounds and ischemia may engage the scalp, the compositions of the present invention further include emollients, surfactants and/or conditioners which are suitable for use on the scalp skin and hair.

The emollients include, but are not limited to, hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like. Other emollients include esters of fatty acids having 10 to 20 carbon atoms, such as including myristic, stearic, isostearic, palmitic, and the like, such as methyl myristate, propyl myristate, butyl myristate, propyl stearate, propyl isostearate, propyl palmitate, and the like. Other emollients include fatty acids having 10 to 20 carbon atoms, including stearic, myristic, lauric, isostearic, palmitic, and the like. Emollients also include fatty alcohols having ten to twenty carbon atoms, such as cetyl, myristyl, lauryl, isostearyl, stearyl and the like.

An emulsifier/surfactant is preferably utilized when formulating the compositions of the present invention for use on hair.

Examples of surfactants include, but are not limited to, spolyoxyalkylene oxide condensation products of hydrophobic alkyl, alkene, or alkyl aromatic functional groups having a free reactive hydrogen available for condensation with hydrophilic alkylene oxide, polyethylene oxide, propylene oxide, butylene oxide, polyethylene oxide or polyethylene glycol. Particularly effective are the condensation products of octylphenol with about 7 to about 13 moles of ethylene oxide, sold by the Rohm & Haas Company under their trademark TRITON 100® series products.

Other ingredients such as, fragrances, stabilizing agents, dyes, antimicrobial agents, antibacterial agents, anti agglomerates, ultraviolet radiation absorbers, and the like are also included in the composition of the present invention which is formulated for use on hair.

A conditioner agent stable to acid hydrolysis, such as a silicone compound having at least one quaternary ammonium moiety along with an ethoxylated monoquat is preferably also utilized in order to stabilize and optionally thicken the composition of the present invention which is formulated for use on hair.

An optional thickener also can be included to improve composition esthetics and facilitate application of the composition to the hair. Exemplary thickeners are methylcellulose, hydroxybutyl methylcellulose, hydroxypropylcellulose, hydroxypropyl methylcellulose, hydroxyethyl ethylcellulose and hydroxyethylcellulose, di (hydrogenated tallow) phthalic acid amide, crosslinked maleic anhydride-methyl vinyl ether copolymer, guar gum, xanthan gum and gum arabic.

The carrier of the conditioning composition is predominantly water, but organic solvents also can be included in order to facilitate manufacturing of the composition or to provide esthetic properties, such as viscosity control. Suitable solvents include the lower alcohols like ethyl alcohol and isopropyl alcohol; glycol ethers, like 2-butoxyethanol, ethylene glycol monoethyl ether, propylene glycol and diethylene glycol monoethyl ether or monomethyl ether; and mixtures thereof. Non-limiting conditioning agents which may be used in opaque conditioners include: stearyltrimethylammonium chloride; behenetrimethylammonium chloride; cetrimonium bromide; soytrimonium chloride; tallowtrimonium chloride; dihyrogenatedtallowdimethylammonium chloride; behentrimethylammonium methosulfate; Peg-2 Oleammonium chloride; dihyrogenatedtallowdimethylammonium bromide; dihyrogenatedtallowdimethylammonium methosulfate; palmityltrimethylammonium chloride; hydrogenated tallowtrimethylammonium chloride; hydrogenated tallowtrimethylammonium bromide; dicetyidimethylammonium chloride; distearyldimethylammonium chloride; dipalmityidimethylammonium chloride; hydrogenated tallowtrimethylammonium methosulfate; cetrimonium to sylate: eicosyltrimethylammonium chloride, and ditallowdimethylammonium chloride.

Materials that can be used to opacify compositions of the invention include fatty esters, opacifying polymers, such as styrene polymers, like OPACIFIER 653™ from Morton, International, Inc.; and fatty alcohols. The following is a non-limiting list of fatty alcohols: cetyl alcohol; stearyl alcohol; cetearyl alcohol; behenyl alcohol; and arachidyl alcohol. Conditioning compositions of the invention which are not clear also can include Lexamine S-13, dicetylammonium chloride, and ceteareth-20

Shampoo formulations are sometimes advantageous for treating scalp skin conditions (e.g. lesions, psoriasis).

The hair shampoo composition of the present invention may be provided in any form selected from liquid, powder, gel and granule as needed. A liquid composition using water or a lower alcohol as a solvent is preferred, with a liquid composition using water being especially preferred. Shampoo compositions which may be used according to the teachings of the present invention are further described in U.S. Pat. Nos. 6,194,363 and 6,007,802.

In a specific embodiment the Erythropoietin and Fibronectin formulations of the present invention comprise about 10-30 µg/mL Erythropoietin and about 100-300 µg/mL Fibronectin, about 0.20% Methyl Paraben, about 9% Laureth and Isoparafin and Polyacrylamide, about 12% Deionized Water, and up to 100% Phosphate Buffer Solution.

Thus embodiments of the present invention comprise topical compositions for promoting angiogenesis and wound healing.

It will be appreciated that compositions of the present invention can be used in combination with other currently practiced therapies such as, without being limited to, photo/light therapy (e.g., Dermanwand™ for Wound Care by National Biological Corp. Beachwood, Ohio) and ultrasound therapy (see e.g., U.S. Pat. No. 6,960,173).

It is expected that during the life of a patent maturing from this application many relevant Erythropoietin and Fibronectin compositions will be developed and the scope of the term Erythropoietin and Fibronectin compositions is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Topical Treatment with Erythropoietin Improves Angiogenesis and Wound Healing in Cutaneous Wounds of Diabetic Rats Materials and Experimental Procedures
Experimental Animals Thirty Male Sprague-Dawley rats, aged 8 weeks (obtained from Harlan, Jerusalem, Israel) were kept in an environment comprising constant temperature and humidity and with an artificial 12-hour light/dark cycle. All rats were allowed free access to food and water. All experimental procedures followed the guidelines of the Animal Care and Use Committee of the Rappaport Faculty of Medicine—Technion Animal Center.

Induction of Diabetes Mellitus

Diabetes was induced by a single 60 mg/kg intraperitoneal injection of streptozotocin (STZ, Sigma Aldrich, St. Louis, Mo., USA), a toxin specific for insulin-producing cells, in saline-sodium citrate buffer (Sigma Aldrich, St. Louis, Mo., USA, pH 4.5). Blood glucose levels were measured using an acute glucometer (FreeStyle, Alameda, Calif., USA). Ten days following subjection to STZ, rats exhibiting blood glucose levels above 300 mg/dL were considered diabetic and were further used in the study.

Generation of Full-Thickness Skin Wounds and Treatments

Diabetic rats with confirmed glucose levels above 300 mg/dL were intraperitoneally anesthetized with Ketamine (100 mg/kg of body weight) and Xylazine (50 mg/kg). The dorsal skin of each rat was shaved, cleaned with an iodine solution and two full-thickness skin wounds (approximately 30 mm in diameter/wound) were created on the right and left sides of each rat back. Diabetic rats were then randomly divided into three treatment groups comprising 10 rats in each group: Group 1) wounds were treated with a basic cream containing saline (designated control group); Group 2) wounds were treated with a cream containing low Erythropoietin concentration (EPO, 500 U/ml; designated low dose group, Cytolab/Peprotech, Rehovot, Israel); and Group 3) wounds were treated with a cream containing high EPO concentration (3000 U/ml; designated high dose group). All rats were treated once daily (for 12 days) with the appropriate cream.

Quantitative Assessment of Wound Healing (Wound Closure)

For computation of the percentage of wound healing, a transparent paper was placed on the location of wound and its shape was drawn on the paper. Next, the wound area was measured by matching the shape of the wound with a graph paper. The percentage of wound healing was calculated by Walker formula (Formula I, hereinbelow). Percentage of wound healing was computed at the beginning of the experiment (day 0) and then again on days 2, 4, 6, 8, 10 and 12.

$$\% \text{ wound area} = \frac{\text{Wound area on day } X}{\text{Wound area on the first day}} \times 100 \quad \text{Formula I}$$

Percentage of wound healing =

100 − percentage of wound area

Histological Examination

Immunohistochemistry was carried out using procedures previously defined. Briefly, rats were sacrificed on day 12 of the experiment and the tissue samples from each group were collected and fixed in 10% formalin. Paraffin-embedded tissues were Sectioned (5 µm) and antigen retrieval was performed using citrate buffer (Sigma Aldrich, St. Louis, Mo., USA). Tissues were treated with a primary antibody anti-CD31 (R&D Systems, MN, USA) and subsequently with an appropriate secondary antibody (R&D Systems, MN, USA). Slides were counterstained with hematoxylin and mounted with coverslips.

To assess angiogenic response, microvessel density (MVD) was calculated. Briefly, three areas with the highest visible blood vessel density per section were selected and the number of blood vessels having a visible lumen was counted at high power field (magnification ×40). A total of 10 to 15 fields in six randomly chosen sections were analyzed for each group. Two independent pathologists performed the histological examination in a blinded fashion.

Determination of VEGF in Wounds

Rats were sacrificed on day 12 of the experiment and the amount of vascular endothelial growth factor (VEGF) present in the wounds was determined by ELISA. Briefly, the wound tissue was homogenized in 1.0 ml of PBS containing Complete Protease Inhibitor Cocktail (Sigma). Homogenates were centrifuged to remove debris, and were filtered through a 1.2 μm pore syringe filter. Analysis was performed with a commercially available human VEGF-specific ELISA kit (R&D Systems, MN, USA). The amount of VEGF was depicted as picogram per wound.

Hydroxyproline (HP) Analysis

HP, found almost exclusively in collagen, was used as an indicator of the amount of collagen present in the wound tissue. Wound HP concentration was determined as previously described [Kwon et al., Exp Biol Med (Maywood) (2007) 232(7):935-41]. Briefly, wound tissue (collected from the sacrificed rats on day 12 of the experiment) was hydrolyzed in 2 ml HCL (6 mol/l) for 4 hours at 130° C. The mixture was then neutralized to pH 7.0 with 2.5 mol/l sodium hydroxide and was diluted 40-fold with deionized water. Next, 2 ml of the diluted mixture was mixed with 1 ml chloramines-T solution (0.05 mol/l) and was incubated for 20 minutes at room temperature. 1 ml of 20% p-dimethylaminobenzaldehyde was then added, and the solution was incubated for 20 minutes at 60° C. The absorbance of each sample was determined at 557 nm by a fluorescent microplate reader, and the amount of HP was determined by comparison to a standard curve.

Statistical Analysis

According to Kolmogorov-Smirnov test, the data had normal distribution. Furthermore, student t-test and ANOVA were used to determine the differences between the different experimental groups. Differences were considered significant when $P<0.05$. Results were given as means of values±standard deviation.

Results

Rat model of diabetes was generated by STZ injection. A gradual increase in blood glucose levels was noted over time and was accompanied by a reduction in body weight. Ten days after subjection to STZ (first day of the study), rats lost 8.7±2.3 g body weight compared to their pre-STZ state, and had further lost weight (lost 19.4±7.1 g body weight compared to their pre-STZ state) 12 days later (as measured on the last day of the study). Blood glucose levels of the diabetic rats used in the present study were consistently higher than 300 mg/dL and did not change by topical application of exogenous cream containing either EPO or vehicle.

Furthermore, due to induction of diabetes, mortality assessment was carried out on the day of animal sacrifice. Results had indicated that seven rats died in the course of this experiment: two rats from the control group, three rats from the high EPO group, and two rats from the low EPO group.

Quantitative Assessment of Wound Healing and Time to Complete Wound Closure

As shown in FIG. 1, significant statistical difference ($P<0.05$) in percentage of wound healing was recorded on day six of the experiment between the high dose EPO and the control rats (treated with vehicle). However, a significant statistically difference ($P<0.05$) between the low dose EPO and the control rats was detected only on day 10 of the experiment. Importantly, a comparison between the two EPO treated groups (low dose EPO and high dose EPO) demonstrated that there were significant statistical differences in percentage of wound healing on days 6, 8, 10 and 12 of the experiment ($P<0.05$).

Furthermore, on day 12 the reduction in wound area was significantly greater in rats treated topically with EPO compared to rats treated with vehicle (data not shown).

Vehicle-treated rats hadn't attained complete wound closure on day 12 whereas EPO treated rats (especially those treated by high dose EPO) achieved a full wound closure on day 12. It is clear from the results that high dose EPO had accelerated the wound healing processes. Taken together, this data remarkably shows the significant clinical value of topical EPO on wound healing.

Histological Results

Using immunohistochemical staining of CD31, an endothelial and vascular cell specific marker, the tissue samples from each treatment group were assessed for microvessel density (MVD) to substantiate neo-vessel formation at the end of treatment. As shown in FIG. 2, assessment of MVD showed a statistically significant difference between rats treated with EPO (low and high dose EPO, 5±1.55 and 8.5±1.05, respectively) compared to control rats treated with vehicle (2.83±0.98; $P<0.05$). Furthermore, topical application of EPO to the wound increased MVD in a dose dependant manner (FIG. 2).

All samples of the control group exhibited avascular areas, ectasic vessels with oedema, perivascular hemorrhage and a marked reduction of capillary ramification. However, wounds of rats treated with topical EPO showed better vascularized areas with an increased expression of CD31 in the wound border and in granulation tissue with numerous endothelial islets. A fewer number of endothelial islets were observed in wounds treated with low dose EPO compared to wounds treated with high dose EPO (data not shown).

Levels of VEGF in Wounds of EPO-Treated and Untreated Rats

As shown in FIG. 3, the levels of the vascular endothelial growth factor (VEGF) were significantly different between treated and untreated wounds. Samples of control rats treated only with vehicle exhibited a very low content of VEGF (0.3±0.02 pg/mg protein). However, samples from low dose EPO treated rats and high dose EPO treated rats exhibited significantly high levels of VEGF (0.9±0.2 and 1.1±0.2 pg/mg protein, respectively). Thus, wound healing was accompanied by a significant increase in VEGF.

Hydroxyproline (HP) Analysis in Wound Tissue

Due to the fact that HP is found almost exclusively in collagen, it was used as an indicator of the amount of collagen present in the wound tissues. As depicted in FIG. 4, topical treatment of wounds with EPO enhanced tissue HP content. Results indicated significant differences between rats treated with either low or high dose EPO (39±5 or 48±7 μg/wound, respectively) and control rats treated with vehicle alone (22±6 μg/wound). EPO treatment resulted in an increase in wound tissue collagen content in a dose dependent manner, substantiating the therapeutic value of the indicated doses of EPO in connective tissue reconstruction and wound healing.

Example 2

Accelerated Cutaneous Wound Healing in Diabetic Mice by Topical Treatment with Erythropoietin and Fibronectin Materials and Experimental Procedures
Experimental Animals Thirty two CD1 nude mice, aged 6 weeks (obtained from Harlan, Jerusalem, Israel) were kept in an environment comprising constant temperature and humidity and with an artificial 12-hour light/dark cycle. All mice were allowed free access to food and water. All experimental procedures followed the guidelines for Animal Care and Use Committee of the Rappaport Faculty of Medicine—Technion Animal Center.

Induction of Diabetes Mellitus

Diabetes was induced by a single 60 mg/kg intraperitoneal injection of streptozotocin (STZ; Sigma Aldrich, St Louis, Mo., USA), a toxin specific for insulin-producing cells, in saline-sodium citrate buffer (Sigma Aldrich, St Louis, Mo., USA, pH 4.5). Blood glucose levels were measured using an acute glucometer (FreeStyle, Alameda, Calif., USA). Five days after STZ injection, mice exhibiting blood glucose levels above 300 mg/dL were defined as diabetic and were further used in the study.

Generation of Full-Thickness Skin Wounds and Treatments

Diabetic mice with confirmed glucose levels above 300 mg/dL were anesthetized with Ketamine (100 mg/kg of body weight) and Xylazine (20 mg/kg) intraperitoneally. The dorsal skin of each mouse was shaved, cleaned with iodine solution, and 2 full-thickness skin wounds (approximately 20 mm in diameter/wound) were created on the right and left sides of each mouse back (FIG. 5A). Diabetic mice were then randomly divided into four treatment groups comprising 8 mice in each group: Group 1) wounds were treated with a basic cream containing saline (Control group, FIG. 5B); Group 2) wounds were treated with a cream containing Erythropoietin (EPO, 3000 U/mL, Cytolab/Peprotech, Rehovot, Israel); Group 3) wounds were treated with a cream containing Fibronectin (FN, 200 µg/mL, Chemicon International Inc., Temecula, Calif., USA); and Group 4) wounds were treated with a cream containing EPO and FN (3000 U/mL and 200 µg/mL, respectively, FIGS. 5B-C). All mice were treated once daily (for 12 days) with the appropriate cream.

Quantitative Assessment of Wound Healing (Wound Closure)

As explained in detail hereinabove in Example 1.

Histological Examination

As explained in detail hereinabove in Example 1.

Determination of VEGF in Wounds

As explained in detail hereinabove in Example 1.

Hydroxyproline (HP) Analysis

As explained in detail hereinabove in Example 1.

Statistical Analysis

As explained in detail hereinabove in Example 1.

Results

Mouse model of diabetes was generated by STZ injection. A gradual increase in blood glucose levels was noted over time and was accompanied by a reduction in body weight (data not shown). Five days after subjection to STZ (first day of the study), mice lost 1.3±0.3 g body weight compared to their pre-STZ state, and had further lost weight (lost 2.2±0.7 g body weight compared to their pre-STZ state) 12 days later (as measured on the last day of the study). Blood glucose levels of the diabetic mice used in the present study were consistently higher than 300 mg/dL and did not change by topical application of exogenous cream containing EPO, FN, EPO/FN or vehicle.

Furthermore, due to induction of diabetes, mortality assessment was carried out on the day of animal sacrifice. Results (data not shown) had indicated that five mice died in the course of this experiment: two mice from the control group, two mice from the EPO group, and one mouse from the EPO/FN group.

Quantitative Assessment of Wound Healing and Time to Complete Wound Closure

Statistical differences between mice treated with EPO compared to mice treated with FN were not significant ($P>0.05$). Whereas, significant statistical difference ($P<0.05$) in the percentage of wound healing was recorded from day 6 to day 12 of the experiment between mice treated by EPO or FN to those treated by vehicle (FIG. 6). However, combination treatment with EPO and FN resulted in significant statistical differences ($P<0.05$) in wound healing as early as 4 days after treatment compared to treatment with EPO, FN or vehicle (FIGS. 6 and 7A-D). A marked increase in wound healing was further recorded on day 6 of the experiment (FIG. 6) when the percentage of healing attained was approximately 86% for mice treated with EPO and FN compared to mice treated with EPO (approximately 46%, $P<0.001$), mice treated with FN (approximately 41%, $P<0.001$) or control mice (approximately 30%, $P<0.001$). Furtheron, on day 8, total wound closure in mice treated with the combination EPO and FN was approximately 96% (FIG. 6 and FIGS. 8A, 8D, 8E and 8G) compared to the other treatment groups where the recorded wound closure was significantly lower (approximately 65% for EPO, approximately 55% for FN and approximately 41% for control mice, FIGS. 6 and 8A-C and 8F-G). Furthermore, on day 12 only mice treated with the combination EPO and FN had achieved full wound closure (approximately 99%, $P<0.001$) whereas all other treatment groups hadn't attained complete wound closure (FIG. 6, FIGS. 9A-F and FIGS. 10A-L). Thus, it is clear from these results that wound treatment with the combination of EPO and FN had greatly accelerated the wound healing processes and had achieved full wound closure.

Histological Results (Microvascular Density)

At the end of treatment (day 12), CD31 immunostaining was performed to confirm new vessel formation (microvessel density, MVD) in tissue samples from each treatment group. As shown in FIG. 11, assessment of MVD showed a statistically significant difference between mice treated with a cream containing EPO compared to control mice treated with vehicle (6.83±1.47 versus 2.33±1.033, respectively, $P<0.01$) but no significant difference was detected between mice treated with a cream containing FN compared to mice treated with vehicle (3.17±0.75 versus 2.33±1.03, respectively, $P>0.05$). However, topical application of a cream containing EPO and FN markedly increased MVD and this increase was statistically significant compared to all the other treatment groups ($P<0.001$).

All tissue samples collected from mice treated with a cream containing FN or treated by vehicle exhibited avascular areas, ectasic vessels with oedema, perivascular hemorrhage and a marked reduction of capillary ramification (data not shown). However, wounds of mice treated with a cream containing EPO or EPO and FN exhibited high vascularized areas with an increased expression of CD31 in the wound border and in granulation tissue with numerous endothelial islets (data not shown).

Levels of VEGF in Wounds of Treated and Untreated Mice

As shown in FIG. 12, the levels of the angiogenic factor (VEGF) significantly differed between the different treatment groups at the end of treatment (day 12). Samples collected from control mice treated with vehicle or mice treated with a cream containing FN exhibited very low levels of VEGF (0.31±0.08 or 0.39±0.12 pg/mg protein, respectively) compared to samples collected from mice treated with a cream containing EPO or EPO and FN (0.74±0.15 or 0.87±0.13 pg/mg protein, respectively, P<0.001). No significant statistical difference was marked between control mice and mice treated with a cream containing FN (P>0.05). Moreover, no significant statistical difference was marked between mice treated with a cream containing EPO and mice treated with a cream containing EPO and FN (P>0.05).

Hydroxyproline (HP) Analysis

HP was used as an indicator of the amount of collagen present in the wound tissues. As depicted in FIG. 13, topical treatment with a cream containing only EPO or only FN equally enhanced HP content in the wounds tissue (44±6.1 or 45.3±7.2 μg/wound, respectively) and was significantly higher compared to treatment with vehicle (16.2±4.7 μg/wound, P<0.001). Conversely, topical treatment with a cream containing both EPO and FN significantly increased HP content in the wound tissue (81±8.8 μg/wound; P<0.001). Thus, by 2 folds compared to treatment with a cream containing only EPO or only FN and by 5 folds compared to treatment with vehicle. Taken together these results indicate that wound treatment with a cream containing both EPO and FN results in a marked increase in collagen and indicates a close interaction between EPO and FN in tissue repair.

Example 3

EPO Upregulates β1-Integrin Expression in HEMCs

Materials and Experimental Procedures

Human Epidermal Microvascular Cell Culture and Experimental Conditions

Primary human epidermal microvascular cells (HEMCs) were purchased from PromoCell (GmbH, Heidelberg, Germany). HEMCs were maintained in human epidermal microvascular endothelial medium (PromoCell, GmbH, Heidelberg, Germany), a modified and optimized DMEM/F-12 (1:1) supplemented with 15 mM HEPES, 10% fetal bovine serum (FBS), growth factor (acidic FGF stabilized with Heparin) and 1% antibiotic solution containing streptomycin, neomycin and penicillin (Biological Industries, Beit Haemek, Israel). All experiments were performed in passages 3-6. HEMCs were seeded in culture dishes coated with fibronectin (10 μg/ml, Chemicon International, Temecula, Calif., USA). Cultured HEMCs were detached by trypsinization and reseeded in fibronectin coated 24× well plates ($2.5 \times 10^5$ cells/well) in triplicates. These cultured HEMCs were treated with escalating doses of EPO (0.01, 0.1 and 1 μg/ml/day) for 3 consecutive days with the culture media replaced on a daily basis. At the end of day 3, HEMCs were detached by trypsinization and tested for expression of β-1 integrin by western blot.

Western Blot Analysis

Collected cells were lysed by RIPA buffer (Sigma Aldrich, St Louis, Mo., USA). 30 μg protein samples were denatured in reducing buffer containing 5% β mercaptoethanol and were separated by electrophoresis on a sodium dodecyl sulfate (12%) polyacrylamide gel. The separated proteins were transferred onto a nitrocellulose membrane using transfer buffer at 200 mA for 1 hour. The membranes were blocked with 5% nonfat dry milk in TBS 0.1% Tween for 1 hour at room temperature, washed and incubated with a primary β-1 integrin antibody (Abcam, Cambridge, UK) in TBS 0.1% Tween overnight at 4° C. After being washed in TBS 0.15% Tween, the membranes were incubated with an appropriate secondary antibody (R&D Systems, MN, USA) for 1 hour at room temperature. After washing, the membranes were analyzed by the enhanced chemiluminescence's system according to the manufacturer's protocol (Amersham, UK).

Results

The expression of β1-integrin, the receptor of fibronectin, was significantly augmented by subjection of HEMCs to EPO (FIGS. 14A-B). β1-integrin expression increased in a dose dependant manner where low dose EPO (0.01 μg/ml) resulted in an expression level of 2.3±0.9, stimuli with 0.1 μg/ml EPO resulted in an expression level of 5.3±1.1, and high dose EPO (1 μg/ml) resulted in an expression level of 18±1.4 (FIG. 14B). The markedly increase in β1-integrin expression in HEMCs, as a result of stimuli with EPO, suggested an increase in the biological effect of FN consequent to EPO hence explaining the synergistic effect of EPO and FN in neoangiogenesis, collagen deposit and wound healing.

Example 4

EPO with and without FN Upregulate Proliferation, Superoxide Dismutase Activity and Aquaporin-3 Expression in Fibroblasts and Keratinocyte Cells Materials and Experimental Procedures Cell Culture Cryopreserved secondary cultures of primary human dermal fibroblasts (NHDF) and of keratinocytes of adult skin (KRCT) were both obtained from Lonza (Lonza, Walkersville, Md., USA). The effect of erythropoietin (EPO) and fibronectin (FN) on NHDF and KRCT cell proliferation was assessed. Briefly, the cells were thawed gently with fibroblasts growth medium (FGM-2, Lonza, Walkersville, Md., USA) and keratinocytes growth medium (KGM, Lonza, Walkersville, Md., USA), respectively, each containing 10% FBS. Cells were seeded into 60 mm plates at a density of $1 \times 10^7$ cells/ml and cultured for 12 days in FGM-2 or KGM, each supplemented with 15% FBS, sodium penicillin G and streptomycin sulfate, in a humidified incubator at 5% $CO_2$ and 95% air at 37° C. The medium was changed every day and the cells were allowed to replicate 3 times. On day 8, all non-adherent cells were removed from the culture and the adherent cells were grown for an additional period of up to 4 days. In the subsequent experiments, the beginning of culture was defined as day 0. On the day of the experiment, cells were lysed by RIPA buffer and lysates were collected for protein expression determination.

[3H]-Thymidine Incorporation Assay

NHDF and KRCT cells were seeded into 6-well plates, coated with or without fibronectin (10 μg/ml), at a density of $1 \times 10^7$ cells/ml and grown for 5 days to reach 60-70% confluence (in FGM-2 and KGM culture mediums, respectively, each supplemented with 15 FBS). The cells were treated with EPO (1, 5 and 10 μg/ml) for 48 hours. 24 hours prior to experimentation, cultures were placed in phenol red-free growth media supplemented with 0.1% FBS. After 24 hours, the cells were placed in phenol red-free growth media containing 7.5% dextran-charcoal stripped FBS. The cells in each well were labeled with 10 μCi of [3H]-thymidine (Shanghai, China) for the last 24 hours of incubation. Cells were then rinsed 3 times with phosphate buffered saline (PBS), 5 minutes each rinse, followed by an additional rinse with 10% trichloroacetic acid, for 30 minutes. Finally, the cells were dissolved in 0.2 ml of 0.2 mol/l NaOH and left overnight at 4° C. Radioactivity was determined by scintillation counting.

Measurement SOD Activity

To determine Superoxide dismutase (SOD) activity, adherent NHDF or KRCT cells of each sample were detached by gentle trypsinization (0.5% trypsin, 0.2% EDTA), counted and lysed by RIPA lysis buffer. This kit utilized tetrazolium salt, WST-1 (4-[3-(4-iodophenyl)-2-(4-nitrophenyl)-2H-5-tetrazolio]-1,3-benzene disulfonate sodium salt) that produced a water-soluble formazan dye upon reduction with SOa. The rate of the reduction with $O^{2-}$ was linearly related to the xanthine oxidase activity, and was inhibited by SOD. The formation of the WST-1 formazan was measured with an absorbance change of 440 nm. The inhibition ratio (%) of each sample was calculated as: Inhibition (%)=100×(H0−H1)/H0, where H0 and H1 represented the peak height observed at the control and the sample containing SOD, respectively.

SDS-PAGE and Western Blot Analysis

Proteins were analyzed by PAGE under non-reducing conditions and electroblotted onto polyvinyldifluoride membranes (Millipore, Molsheim, France). The membranes were incubated for 2 hours with AQP3 antibodies diluted 1:200 (Calbiochem, Nottingham, UK) or actin antibodies diluted 1:1000 (Calbiochem) in 0.1 M Tris-buffered saline containing 5% non-fat dry milk and 0.05% Tween 20. The membranes were then rinsed in Tris-buffered saline/non-fat dry milk/Tween 20 and incubated for 1 hour with horseradish peroxidase-conjugated goat anti-rabbit Igs diluted 1:2000 (R&D systems). Finally, the membranes were rinsed in Tris buffered saline and the reaction product was detected using a chemiluminescence detection kit (Amersham Biosciences, Freiburg, Germany). The resulting signals were analyzed by densitometry and the results were expressed as the ratio of the optical density of the AQP3-corresponding band to that of actin.

Statistical Analysis

Data were expressed as means±SEM or as percentage of control. Statistical comparisons of the results were made using analysis of variance (ANOVA). Significant differences (P<0.05) between the means of the control and test groups were analyzed by Dunnett's test. *P<0.05, P<0.01, *P<0.001.

Results

Keratinocytes of adult skin (KRCT) were treated with erythropoietin (EPO) with or without fibronectin (FN) to assess its effect on cell proliferation. As is evident from FIG. 15A, treatment of KRCT with EPO (especially 10 μg) lead to a significant increase in cell proliferation. Furthermore, the additions of FN to these cells lead to a synergistic increase in cell proliferation (FIG. 15B).

Superoxide dismutase (SOD) is a membrane enzyme that scavenges the free radicals superoxide anions in the intra or extracellular space. Reducing the superoxide anions in the epidermis and dermis layers is essential to preserve skin from damage and aging. SOD can be a major factor in attenuating these detrimental effects induced by the accumulation of superoxide anions. As is evident from FIG. 16A, culturing primary human dermal fibroblasts (NHDF) or KRCT cells with EPO upregulates SOD (antioxidant activity). Additions of FN to the cell cultures synergistically upregulates SOD activity by about 1.5 fold (FIG. 16B).

One of the major characteristics of human skin aging is the dehydration of the skin. Water movement across plasma membrane occurs via diffusion through lipid bilayer and via aquaporins (AQPs). Aquaporin-3 (AQP3) is a membrane transport protein that facilitates water and glycerol transport across cell plasma membranes in the basal layer of keratinocytes in normal skin. Healing of skin wounds is a multi-step process involving the migration and proliferation of basal keratinocytes in epidermis, which strongly express the water/glycerol-transporting protein AQP3. Therefore, protein extracts of all the treated NHDF or KRCT samples were used to determine AQP3 expression. As is evident from FIGS. 17A-B addition of EPO to the NHDF or KRCT cell cultures lead to an increase in AQP3 expression (FIG. 17A), this increase was significantly increased when the cells were co-cultured with FN (FIG. 17B)

Example 5

EPO Upregulates Bcl-xL Expression and Decreases Apoptosis Sensitivity

Materials and Experimental Procedures

Experimental Animals

As explained in detail hereinabove in Example 1.

Apoptosis Analysis by Western Blot for Bax, and Bcl-$x_L$

Western blots were performed. Briefly, samples of the wounded tissues of each group were obtained at day 12 of the experiment, samples were homogenized and treated with RIPA buffer (50 mM Tris, 150 mM NaCl, 2.5 mg/ml deoxycholic acid, 1 mM EGTA, 10 μg/ml Nonidet-40, pH 7.4, supplemented with protease inhibitors: 2.5 μg/ml leupeptin, 0.95 μg/ml aprotinin and 2.5 mM phenylmethylsulfonyl fluoride). Proteins from whole tissue lysates were loaded onto 12% SDS-PAGE (40 μg/well). Fractionated proteins in gels were either stained with Coomassie Blue R-250 or transferred to nitrocellulose membranes to perform Western blots. 5% low fat milk in TBS-T buffer (50 mM Tris (hydroxymethyl) aminomethane, 175 mM NaCl, adjusted to pH 7.5 with HCl and supplemented with 0.1% Tween 20) was used as blocking solution. Membranes were incubated with mouse monoclonal anti Bax (Clone YTH6A7) and mouse monoclonal anti Bcl-$x_L$ (Clone YTH2H12) primary antibodies both from (R&D Systems). Antibodies were diluted 1/500 in blocking solution. Conditions of incubation were optimized for each antibody. Secondary antibody: IgG donkey anti-mouse horseradish peroxidase (HRP) labeled (R&D Systems) was diluted 1/2000 in blocking solution. Incubations were performed for 1 hour at room temperature. Results were expressed as mean±S.E.M Arbitrary Units (AU) obtained from the ratio between the densitometric units of the protein under study and total μg of proteins loaded.

Statistical Analysis

According to Kolmogorov-Smirnov test, the data had normal distribution. Furthermore, student t-test and ANOVA were used to determine the differences between the different experimental groups. Differences were considered significant when P<0.05. Results were given as means of values±standard deviation.

Results

EPO inhibits apoptosis by up-regulating the anti-apoptotic protein Bcl-xL [Dolzing (2001)]. In addition, previous studies have shown that alterations in the ratio between pro-apoptotic and anti-apoptotic members of the Bcl-2 family, rather than the absolute expression level of any single member, determines apoptotic sensitivity [Zhang (2000)].

As is depicted in FIGS. 18A-B, topical treatment with EPO did not inhibit the expression of Bax. In fact, this pro-apoptotic protein remained unchanged despite the increment in EPO dose (ANOVA test revealed no significant difference between the groups, P=NS, FIG. 18A). Nevertheless, Bcl-xL was strongly up regulated in diabetic wounds treated by EPO compared to control diabetic wounds (FIG.

18A). A cream containing EPO up regulated this anti-apoptotic protein dose dependently in the diabetic wounds (ANOVA test; control vs. low dose EPO, control vs. high dose EPO and low dose EPO vs. high dose EPO; P<0.05, P<0.001, and P<0.05; respectively; FIG. 18A). Apoptotic sensitivity was determined by the ratio between the mean of pro-apoptotic protein expression Bax and the mean of anti-apoptotic protein expression Bcl-xL. As depicted in FIG. 18B, apoptosis decreased significantly and dose dependently following EPO treatment, ANOVA analysis revealed significant differences between the three groups (P<0.05).

Example 6

Formulation of Creams Containing EPO, FN or Both

Materials and Experimental Procedures
Formulation of EPO and FN
A=Erythropoietin (EPO)
B=Fibronectin (FN)
For cream A: 25 µg/g (2.50 mg % of final preparation)
For cream B: 250 µg/g (25 mg % of final preparation)
For cream A/B (combination cream): 25 µg/g (2.50 mg % of final preparation) and 250 µg/g (25 mg % of final preparation)

| Formula | |
| --- | --- |
| 1. Active Ingredients | as needed |
| 2. Methyl Paraben | 0.20% |
| 3. Laureth & Isoparafin & Polyacrylamide | 9% |
| 4. Deionized Water | 12% |
| 5. Phosphate Buffer Solution to | 100% |

Method:
1. Calculate the amounts needed for preparation.
2. Weigh #2 and #3 in dry, clean, glass containers.
3. Assemble the following:
   1. Add #2 to #4 and stir.
   2. Heat the mixture to 55-60° C. in a glass container while stirring till #2 dissolves. Chill solution to room temperature.
3. Add 70% of #5 and stir.
4. Add Active ingredient/s (#1) to solution and stir.
5. Add #3 to solution gradually while stirring.
6. Add the rest of #5 (to obtain needed volume) and stir continuously until a homogeneous preparation is obtained
7. Store in a tight, closed, dark container at 4° C.

Results

A white, opaque, semi-solid preparation is obtained. The pH of the obtained preparations is about 6.40. Preparation may be used fresh.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A pharmaceutical composition comprising about 10-30 µg/mL Erythropoietin, about 100-200 µg/mL Fibronectin, about 0.20% Methyl Paraben, about 9% laureth and isoparaffin and polyacrylamide, about 12% deionized water and a phosphate buffer solution.

* * * * *